United States Patent
Hochrein et al.

(10) Patent No.: US 8,961,998 B2
(45) Date of Patent: *Feb. 24, 2015

(54) IMMEDIATE PROTECTION AGAINST PATHOGENS VIA MVA

(75) Inventors: Hubertus Hochrein, Munich (DE); Meredith O'Keeffe, Munich (DE)

(73) Assignee: Bavarian Nordic A/S, Kvistgaard (DK)

(*) Notice: Subject to any disclaimer, the term of this patent is extended or adjusted under 35 U.S.C. 154(b) by 261 days.

This patent is subject to a terminal disclaimer.

(21) Appl. No.: 13/589,273

(22) Filed: Aug. 20, 2012

(65) Prior Publication Data

US 2013/0216572 A1 Aug. 22, 2013

Related U.S. Application Data

(63) Continuation of application No. 12/596,204, filed as application No. PCT/EP2008/003367 on Apr. 25, 2008, now Pat. No. 8,268,328, which is a continuation-in-part of application No. 12/026,612, filed on Feb. 6, 2008, now Pat. No. 8,268,327.

(60) Provisional application No. 60/935,920, filed on Sep. 6, 2007, provisional application No. 60/924,048, filed on Apr. 27, 2007.

(51) Int. Cl.
| | |
|---|---|
| *A61K 39/285* | (2006.01) |
| *A61K 39/12* | (2006.01) |
| *A61K 39/00* | (2006.01) |

(52) U.S. Cl.
CPC ............. *A61K 39/285* (2013.01); *A61K 39/12* (2013.01); *A61K 2039/5254* (2013.01); *A61K 2039/58* (2013.01); *C12N 2710/24134* (2013.01)
USPC ..................................................... 424/232.1

(58) Field of Classification Search
CPC ................... A61K 2039/5254; A61K 39/285; C12N 2710/24134
See application file for complete search history.

(56) References Cited

U.S. PATENT DOCUMENTS

| | | | |
|---|---|---|---|
| 6,761,893 B2 | 7/2004 | Chaplin et al. | |
| 7,972,605 B2 | 7/2011 | Patel et al. | |
| 8,268,327 B2 * | 9/2012 | Hochrein et al. | 424/232.1 |
| 8,268,328 B2 * | 9/2012 | Hochrein et al. | 424/232.1 |
| 2003/0202988 A1 | 10/2003 | Chaplin | |
| 2003/0206926 A1 | 11/2003 | Chaplin et al. | |
| 2004/0175398 A1 | 9/2004 | Moyer | |
| 2010/0129404 A1 | 5/2010 | Hochrein et al. | |
| 2011/0142877 A1 | 6/2011 | Chaplin et al. | |
| 2011/0177114 A1 | 7/2011 | Hochrein et al. | |

FOREIGN PATENT DOCUMENTS

| | | |
|---|---|---|
| WO | WO0242480 A1 | 5/2002 |
| WO | WO03088994 A1 | 10/2003 |
| WO | WO03097845 A1 | 11/2003 |
| WO | WO2004087201 A2 | 10/2004 |
| WO | WO2006089690 A1 | 8/2006 |

OTHER PUBLICATIONS

Didierlaurent et al., Attenuated poxviruses expressing a synthetic HIV protein stimulate HLA-A2-restricted cytotoxic T-cell responses, Vaccine 22: 3395-3403, 2004.
Veryard et al., Interscience conference on Antimicrobial Agents and Chemotherapy 44th Annual Meeting, IDrugs 7(12 ): 1055-1057, 2004.
Anon, Imvamune IND Receives Approval, Drug News Perspect. 17 (5):313, 2005.
Drexler et al., Modified vaccinia virus Ankara as antigen delivery system:how can we best use its potential?, Current Opinion in Biotechnology 15(6):506-512, 2004.
Vollmar et al, 3rd Generation Smallpox Vaccine ImvamuneTM (MVA-BN), Presented at the 2005 ASM Biodefense Meeting, Mar. 3, 2005.
Stittelar et al., Modified Vaccnia Virus Ankara Protects Macaques against Respiratory Challenge with Monkeypox Virus, Journal of Virology 79(12):7845-7851, 2005.
Wyatt et al., Highly Attenuated smallpox vaccine protects mice with and without immune deficiencies against pathogenic vaccinia virus challenge, Proc. Natl. Acad. Sci. 101 (13):4590-4595, 2004.
Stittelar et al., Antiviral Treatment is more effective than smallpox vaccination upon lethal monkeypoxvirus infection, Nature 439:745-748, 2006.
Staib et al., Short-term, but not post-exposure, protection against lethal orthopoxvirus challenge after immunization with modified vaccinia virus Ankara, Journal of General Virology 87:2917-2921, 2006.
Mortimer, Can Postexposure Vaccination against Smallpox Succeed? Confronting Biological Weapons 36: 622-629, 2003.
Anon, Vaccinia (Smallpox) Vaccine Recommendations of the Advisory Committee on Immunization Practices (ACIP), MMWR 50: 1-26 (Jun. 22, 2001).
Anon, Smallpox Fact Sheet, Department of Health and Human Services, centers for Disease Control and Prevention, Mar. 31, 2003.
Anton Mayr, Smallpox vaccination and bioterrorism with pox viruses, Comparative Immunology Microbiology and Infectious Diseases 26:423-430 (2003).
Massoudi et al. Effectiveness of Postexposure vaccination for the prevention of smallpox: Results of a Delphi analysis, Journal of Infectious Diseases 188:973-976 (2003).
Harrer et al. Therapeutic vaccination of HIV-1-infected patients on HAART with a recombinant HIV-1 nef-expressing MVA: safety, immunogenicity and influence on viral load during treatment interruption, Antiviral Therapy 10:285-300 (2005).

(Continued)

*Primary Examiner* — Mary E Mosher
(74) *Attorney, Agent, or Firm* — Law Office of Salvatore Arrigo and Scott Lee, LLP

(57) ABSTRACT

The invention relates to methods and kits comprising poxviruses including, but not limited to modified vaccinia virus Ankara (MVA) and uses thereof to provide immediate protection against pathogens. Poxviruses including, but not limited to MVA can be delivered to a host animal just prior to or after exposure to a pathogen and provide protection against the pathogen.

18 Claims, 13 Drawing Sheets

(56) References Cited

OTHER PUBLICATIONS

Ondondo et al. Immunisation with recombinant modified vaccinia virus Ankara expressing HIV-1 gag in HIV-1-infected subjects stimulates broad functional CD4+ T cell responses, European Journal of Immunology 36:2585-2594 (2006).

Samuelsson et al. Survival of lethal poxvirus infection in mice depends on TLR9, and therapeutic vaccination provides protection, Journal of Clinical Investigation 118:1776-1784 (2008).

Kretzschmar et al., Ring Vaccination and Smallpox Control, Emerging Infectious Diseases 10:832-841 (2004).

America Academy of Pediatrics, Policy Statement—Smallpox Vaccine, Pediatrics 110;841-845. (2002).

Veryard et al, Antiviral Therapeutics, IDrugs 2004 7(12):1055-1057.

Lauterbach et al., Immune Requirements of Post-Exposure Immunization with Modified Vaccinia Ankara of Lethally Infected Mice, PLoS ONE 5(3): e9659. doi:10.1371/journal.pone.0009659 (2010).

Esteban et al., Ectromelia virus: the causative agent of mousepox, Journal of General Virology (2005), 86, 2645-2659.

Chapman et al., Animal Models of Orthopoxvirus Infection, Veterinary Pathology 47(5) 852-870 (2010).

Paran et al., Postexposure Immunization with Modified Vaccinia Virus Ankara or Conventional Lister Vaccine Provides Solid Protection in a Murine Model of Human Smallpox, The Journal of Infectious Diseases 2009; 199:39-48.

Bavarian Nbordic, Presentation of May 27, 2004 (downloaded from http://www.finansanalytiker.dk/dokumenter/presentationer/2004/2004_Virksomhedsdag/Bavarian.pdf on May 23, 2011).

Vilsmeier, (Berliner and Munchener Tierarztliche Wochenschrift 112(9): 329-333, 1999).

* cited by examiner a b

| | ECTV |
|---|---|
| ■ | 1E+04 + MVA |
| ▲ | 1E+03 + MVA |
| ◆ | 1E+02 + MVA |
| ⊠ | 1E+02, no MVA |

Figure 6

IMMEDIATE PROTECTION AGAINST PATHOGENS VIA MVA

CROSS-REFERENCE TO RELATED APPLICATIONS

This application is a continuation of application Ser. No. 12/596,204, filed Nov. 16, 2009, which is the U.S. National Stage of International Application No. PCT/EP2008/003367, filed Apr. 25, 2008, which is a continuation-in-part of U.S. application Ser. No. 12/026,612, filed Feb. 6, 2008. Appln. No. PCT/EP2008/003367 filed Apr. 25, 2008, claims the benefit of U.S. Provisional Appln. No. 60/935,920, filed Sep. 6, 2007, and U.S. Provisional Appln. No. 60/924,048, filed Apr. 27, 2007. All of these applications are incorporated herein by reference.

FIELD OF THE INVENTION

The invention relates to the use of modified vaccinia virus Ankara (MVA) to provide immediate protection against pathogens.

BACKGROUND OF THE INVENTION

Poxviruses, including the causative agent of smallpox, Variola virus (VARV), are highly pathogenic double stranded (ds) DNA viruses. It is estimated that smallpox has caused more than 300 million deaths in the 20th century alone. Even though traditional vaccination programs have eradicated VARV as a natural pathogen, it remains that enhancing the knowledge of mechanisms of its infections and/or protection may be essential given the scenarios of zoonotic poxvirus infections (e.g. monkeypox), the re-emergence of VARV by accidental release, or the possibility of terrorist attacks with poxviruses.

The genus Orthopoxvirus contains several related viruses based on genetic similarity and immunological cross-reactivity, including VARV, the causative agent of human smallpox, ectromelia virus (ECTV) causing mousepox, cowpox virus (CPXV), monkeypox virus (MPXV), camelpox virus (CMPV), and vaccinia virus (VACV). Among these ECTV, MPXV, and VACV are used in animals as model infections for human smallpox. A number of VACV strains have been used in mice and large amounts of evidence on the immune responses induced and on the immune suppressing mechanisms employed by poxviruses have been elucidated with VACV. However, VACV is not a natural pathogen of mice and high doses are needed to lethally infect mice, even though mouse-adapted strains like VACV Western Reserve (WR) are commonly used (Williamson et al., *J. Gen. Virol.* 71:2761-2767 (1990)). MPXV in monkeys has the advantage that monkeys are evolutionarily much closer to humans. However, as with the VACV model in mice, non-physiological high viral doses are needed to lethally infect monkeys. Therefore, both animal models are regarded to reflect more the late stage of a VARV infection in humans (Fenner, F., Henderson, D. A., Arita, I., Jezek, Z., & Ladnyi, I. D. *Smallpox and its eradication*. Geneva: World Health Organization (1988); Mortimer, P. P. *Clin. Infect. Dis.* 36, 622-629 (2003)). Among the orthopoxvirus infection models, ECTV infection of mice stands out because it is a species-specific virus infecting its natural host and can cause fatal outcomes after inoculation with low virus doses, features that have also been described in VARV infection of humans (Fenner et al., 1988; Esteban, D. J., and Buller, R. M., *J. Gen. Virol.* 86:2645-2659 (2005)). For these reasons, this model is the closest model to human infection by VARV.

Pathogens are detected by the immune system via pattern recognition receptors (PRR). Among the latter is the family of Toll-like receptors (TLR). TLR7, and TLR8 and 9 recognize the nucleic acids RNA and DNA, respectively (Hemmi, H. et al., *Nature* 408, 740-745 (2000); Diebold, S. S. et al. *Science* 303, 1529-1531 (2004); Heil, F. *Science* 303, 1526-1529 (2004)). Double stranded DNA (dsDNA) viruses, like herpesviruses or adenoviruses, can be detected via TLR9-dependent pathways (Basner-Tschakarjan, E. et al., *J. Gene Med.* 8, 1300-1306 (2006); Lund, J. et al., *J. Exp. Med.* 198, 513-520 (2003); Krug, A. et al. *Blood* 103, 1433-1437 (2004); Hochrein, H. et al. *Proc. Natl. Acad. Sci. U.S.A.* 101, 11416-11421 (2004); Tabeta, K. et al. *Proc. Natl. Acad. Sci. U.S.A.* 101, 3516-3521 (2004)). However, potent alternative recognition pathways exist, possibly explaining why previous viral infection studies have demonstrated no or only mild increases of susceptibility in the absence of TLR9 (Hochrein, H. et al. *Proc. Natl. Acad. Sci. U.S.A.* 101, 11416-11421 (2004); Krug, A et al. *Blood* 103, 1433-1437 (2004); Zhu, J. et al. *Blood* 109, 619-625 (2007); Delale, T. *J. Immunol.* 175, 6723-6732 (2005); Tabeta, K. et al. *Proc. Natl. Acad. Sci. U.S.A.* 101, 3516-3521 (2004)).

Whereas many TLR are located at the outer membrane of the cell to monitor the extracellular space for danger signals like bacterial cell wall components, a group of TLR consisting of TLR 3, 7, 8, and 9 are associated with the endosome and monitor the endosomal lumen for nucleic acids (Wagner, H., and Bauer, S., *J. Exp. Med.* 203:265-268 (2006)). The TLR 3, 7, and 8 recognize RNA, whereas TLR9 recognizes DNA (Diebold et al., *Science* 303: 1529-153 (2004); Heil et al., *Science* 303:1526-1529 (2004); Hemmi et al., *Nature* 408: 740-745 (2000); Alexopoulou et al., *Nature* 413:732-738 (2001)).

Expression of TLR9 differs within species. Whereas in humans B-cells and plasmacytoid DC (pDC), but not conventional DC (cDC), express and respond to TLR9 stimulation, TLR9 expression in mice is less restricted. Besides B-cells and pDC, mouse cDC and even macrophages are known to express TLR9 and respond to TLR9 ligation (Hochrein et al., *Hum. Immunol.* 63:1103-1110 (2002)). The natural ligand for TLR9 was originally defined to be genomic bacterial DNA, whereas oligonucleotides containing unmethylated CpG motifs adjoined by species specific motifs and often phosphorothioate-stabilized (CpG-ODN), were established as artificial ligands for TLR9 (Hemmi et al., 2000; Bauer et al., *Proc. Natl. Acad. Sci. U.S.A* 98:9237-9242 (2001)).

Meanwhile, the list of CpG containing natural and artificial ligands has increased to bacterial plasmid DNA and several types of CpG-ODN with differences in their chemical composition, as well as drastic differences in biological effects including IFN-I inducing capacity (Spies et al., *J. Immunol.* 171:5908-5912 (2003); Krieg, A. M. *Nat. Rev. Drug Discov.* 5:471-484 (2006)). Under conditions of enhanced uptake, non CpG-containing or fully methylated DNA as well as vertebrate DNA have also been shown to act as TLR9 agonists (Yasuda et al., *J. Immunol.* 174:6129-6136 (2005); Means et al., *J. Clin. Invest* 115:407-417 (2005)).

Poxviruses have evolved multiple strategies for immune suppression, substantiated by the fact that poxvirus genomes encode numerous molecules with immunosuppressive function. Among these are soluble cytokine and chemokine receptors and a multitude of molecules that interfere with intracellular signaling cascades (Seet, B. T. et al. *Annu. Rev. Immunol.* 21, 377-423 (2003)). Recently, molecules expressed by poxviruses have been shown to target members of the TLR signaling cascade, suggesting a role for TLR-dependent recognition pathways for poxviruses (Bowie, A. et al. *Proc. Natl. Acad. Sci. U.S.A.* 97, 10162-10167 (2000)). In fact, a role for TLR2 in the recognition of vaccinia viruses (VACV) was proposed (Zhu, J. et al. *Blood* 109, 619-625 (2007)).

Modified Vaccinia Ankara (MVA) virus is related to Vaccinia virus, a member of the genera Orthopoxvirus in the family of Poxviridae. MVA has been generated by 516 serial passages on chicken embryo fibroblasts of the Ankara strain of vaccinia virus (CVA) (for review see Mayr, A., et al. *Infection* 3, 6-14 (1975)). As a consequence of these long-term passages, the resulting MVA virus deleted about 31 kilobases of its genomic sequence and, therefore, was described as highly host cell restricted to avian cells (Meyer, H. et al., *J. Gen. Virol.* 72, 1031-1038 (1991)). It was shown, in a variety of animal models, that the resulting MVA was significantly avirulent (Mayr, A. & Danner, K. *Dev. Biol. Stand.* 41: 225-34 (1978)). Additionally, this MVA strain has been tested in clinical trials as vaccine to immunize against the human smallpox disease (Mayr et al., *Zbl. Bakt. Hyg. I, Abt. Org. B* 167, 375-390 (1987), Stickl et al., *Dtsch. Med. Wschr.* 99, 2386-2392 (1974)). These studies involved over 120,000 humans, including high risk patients, and proved that, compared to Vaccinia based vaccines, MVA had diminished virulence or infectiousness while it maintained good immunogenicity. In the decades that followed, MVA has been engineered to use it as viral vector for recombinant gene expression and as a recombinant vaccine (Sutter, G. et al., *Vaccine* 12: 1032-40 (1994)).

In this respect, it is most astonishing that, even though Mayr et al. demonstrated during the 1970s that MVA is highly attenuated and avirulent in humans and mammals, some recently reported observations (Blanchard et al. *J. Gen. Virol.* 79, 1159-1167 (1998); Carroll & Moss, *Virology* 238, 198-211 (1997); U.S. Pat. No. 5,185,146; Ambrosini et al., *J. Neurosci. Res.* 55(5), 569 (1999)) have shown that MVA is not fully attenuated in mammalian and human cell lines since residual replication might occur in these cells. It is assumed that the results reported in these publications have been obtained with various strains of MVA, since the viruses used essentially differ in their properties, particularly in their growth behavior in various cell lines.

Growth behavior is recognized as one of several indicators for virus attenuation. Generally, a virus strain is regarded as attenuated if it has lost its capacity or only has reduced capacity to reproductively replicate in host cells. The above-mentioned observation, that MVA is not completely replication incompetent in human and mammalian cells, brings into question the absolute safety of MVA as a human vaccine or a vector for recombinant vaccines.

Particularly, for a vaccine as well as for a recombinant vaccine, the balance between the efficacy and the safety of the vaccine vector virus is extremely important.

As described in WO publication 02/42480, novel MVA strains with enhanced safety have been developed. These strains are characterized by having at least one of the following advantageous properties:
  (i) capability of reproductive replication in vitro in chicken embryo fibroblasts (CEF), but no capability of reproductive replication in a human cell line, as in the human keratinocyte cell line HaCaT, the human embryo kidney cell line 293, the human bone osteosarcoma cell line 143B, and the human cervix adenocarcinoma cell line HeLa;
  (ii) failure to replicate in a mouse model that is incapable of producing mature B and T cells and as such is severely immune compromised and highly susceptible to a replicating virus; and
  (iii) induction of at least the same level of specific immune response in vaccinia virus prime/vaccinia virus boost regimes when compared to DNA-prime/vaccinia virus boost regimes.

One of the developed strains has been deposited at the European Collection of Animal Cell Cultures (ECACC), Vaccine Research and Production Laboratory, Public Health Laboratory Service, Centre for Applied Microbiology and Research, Porton Down, Salisbury, Wiltshire SP4 0JG, United Kingdom, with the deposit number V00083008. This strain is referred to as "MVA-BN" throughout the specification of WO 02/42480.

The terms "not capable of reproductive replication" or "replication incompetent" mean that the virus shows an amplification ratio of less than 1 in human cell lines, such as the cell lines 293 (ECACC No. 85120602), 143B (ECACC No. 91112502), HeLa (ATCC No. CCL-2) and HaCat (Boukamp et al., *J. Cell Biol.* 106(3): 761-71 (1988)), under the conditions as outlined in Example 1 of WO 02/42480 for some specific MVA strains.

According to WO 02/42480, "failure to replicate in vivo" refers to viruses that do not replicate in humans and in the mice model as described in the WO 02/42480 publication.

There have been numerous reports suggesting that prime/boost regimes using MVA as a delivery vector induce poor immune responses and are inferior to DNA-prime/MVA-boost regimes (Schneider et al., *Nat. Med.* 4; 397-402 (1998)). In all these studies, MVA strains have been used that are different from the vaccinia viruses as developed according to WO 02/42480. As an explanation for the poor immune response obtained when MVA was used for prime and boost administration, it has been hypothesized that antibodies generated to MVA during the prime-administration neutralize the MVA given in the second immunization, preventing an effective boost of the immune response. In contrast, DNA-prime/MVA-boost regimes are reported to be superior at generating high avidity responses, because this regime combines the ability of DNA to effectively prime the immune response with the properties of MVA to boost this response in the absence of a pre-existing immunity to MVA. Clearly, if a pre-existing immunity to MVA and/or vaccinia prevents boosting of the immune response, then the use of MVA as a vaccine or therapeutic would have limited efficacy, particularly in the individuals that have been vaccinated against smallpox. However, the vaccinia virus strains according to WO 02/42480, as well as corresponding recombinant viruses harbouring heterologous sequences, can be used to efficiently first prime and then boost immune responses in native animals as well as in animals with a pre-existing immunity to poxviruses. Thus, the developed strains as described in WO 02/42480 induce at least substantially the same level of immunity in vaccinia virus prime/vaccinia virus boost regimes compared to DNA-prime/vaccinia virus boost regimes.

A vaccinia virus is regarded as inducing at least substantially the same level of immunity in vaccinia virus prime/vaccinia virus boost regimes when compared to DNA-prime/vaccinia virus boost regimes if the CTL response as measured in one of the two, or even in both assays, as described in WO 02/42480 is at least substantially the same in vaccinia virus prime/vaccinia virus boost regimes when compared to DNA-prime/vaccinia virus boost regimes.

The growth behavior of the vaccinia viruses developed according to WO 02/42480, in particular the growth behavior of MVA-BN®, indicates that the strains are far superior to any other so far characterized MVA isolate regarding attenuation in human cell lines and failure of in vivo replication. The strains are therefore ideal candidates for the development of safer products such as vaccines or pharmaceuticals.

An immune response is raised by the immune system when a foreign substance or microorganism enters the organism. By definition, the immune response is divided into a specific and an unspecific reaction, although both are closely cross linked. The unspecific immune response is the immediate defence against a wide variety of foreign substances and infectious agents. The specific immune response is the defence raised after a lag phase, when the organism is challenged with a substance for the first time. The specific immune response is highly efficient, and is responsible for the fact that an individual who recovers from a specific infection is protected against this specific infection. Thus, a second infection with the same or a very similar infectious agent causes much milder symptoms or no symptoms at all, since there is already a "pre-existing immunity" to this agent. Such immunity and the immunological memory persist for a long time, in some cases even lifelong. Accordingly, the induction of an immunological memory can result from vaccination.

The "immune system" means a complex organ involved in the defence of the organism against foreign substances and micro-organisms. The immune system comprises a cellular part comprising several cell types, such as, e.g., lymphocytes and other cells derived from white blood cells, and a humoral part comprising small peptides and complement factors.

Traditional vaccination strategies are able to induce effective and long lasting protection by inducing adaptive immune responses (antibodies, CTL). However, substantial protection can only be achieved after several days to months, optimally with a boost regime, which leaves the individual susceptible to infection during that time.

MVA is a non-replicating virus in humans, which can be administered to people with various degrees of immune deviation (HIV, allergies, atopic dermatitis, certain drug treatments), even via systemic application routes. In these cases of immune deviation, a specialized anti-viral immune cell population (pDC) is reduced in number or affected in its functional properties, which may increase the risk for viral infection.

The current view of protection against deadly poxviruses is via vaccinations. For these approaches, individuals are exposed to an attenuated (less pathogenic) poxvirus before the potential exposure to a pathogenic poxvirus. Vaccination induces adaptive immune responses like Killer T cells (CTL) and antibodies and a memory against the related vaccinating virus. This results in some reactivity against the pathogenic virus, leading to protection and quick resurrection of the memory responses upon repeated exposure. However, adaptive immune responses need time to develop, and are optimal after boosting the immune response with repetitive application of the vaccinating virus.

Recently, it was reported that, employing MVA as vaccinating virus several days (at latest 2 days) before exposure with the Vaccinia virus Western Reserve strain (VV-WR), some protection can be achieved (WO2006/089690, which is hereby incorporated by reference in its entirety). Similar results have been published by another group, which further demonstrated post-exposure treatment failed to protect animals. (Staib, C. et al. J. Gen. Virol 87, 2917-2921 (2006)). The protection levels were 1×LD50 if vaccinated 2 days before exposure to VV-WR and 12.5×LD50 if vaccinated 3 days before exposure to VV-WR. (Id.)

Stittelaar et al., Nature 439:745-748 (2006) compared the effects of antiviral treatment and smallpox vaccination upon lethal monkeypox virus infection. They reported that when monkeys were vaccinated 24 h after monkeypox virus infection, using a standard human dose of a currently recommended smallpox vaccine (Elstree-RIVM), no significant reduction in mortality was observed.

Thus, there is a need in the art for reagents and methods for immediate protection against pathogens, such as smallpox.

BRIEF SUMMARY OF THE INVENTION

The invention encompasses a method for inducing an immune response against an infectious agent in an animal, comprising administering to the animal an immunogenic composition comprising a poxvirus between 36 hours prior to infection with the infectious agent and 72 hours after infection with the infectious agent.

Furthermore, the invention encompasses the use of a poxvirus for the preparation of an immunogenic composition comprising said poxvirus for inducing an immune response against an infectious agent in an animal, wherein said immunogenic composition is to be administered to the animal between 36 hours prior to infection with the infectious agent and 72 hours after infection with the infectious agent.

The invention also encompasses a poxvirus for inducing an immune response against an infectious agent in an animal. Furthermore, the invention encompasses an immunogenic composition comprising said poxvirus for inducing an immune response against an infectious agent in an animal. In a preferred embodiment, said poxvirus or immunogenic composition comprising said poxvirus is to be administered to the animal between 36 hours prior to infection with the infectious agent and 72 hours after infection with the infectious agent.

In a preferred embodiment, the poxvirus is administered between 36 hours prior to infection with the infectious agent and 48 hours after infection with the infectious agent.

In a preferred embodiment, the poxvirus is replication incompetent in the animal.

In a preferred embodiment, the poxvirus is a Modified Vaccinia Virus Ankara (MVA).

In a preferred embodiment, the animal is a human.

In a preferred embodiment, the infectious agent is a replication competent poxvirus.

In one embodiment, the MVA is administered in a dose of $10^5$ to $5 \times 10^8$ TCID50. In a preferred embodiment, the MVA is administered intravenously, intranasally, intramuscularly, or subcutaneously.

In one embodiment, the MVA is MVA-BN®. The MVA can be a recombinant MVA and can comprise at least one heterologous nucleic acid sequence coding for at least one antigenic epitope. The antigenic epitope can be an antigenic epitope of the infectious agent. The infectious agent can be selected from viruses, fungi, pathogenic unicellular eukaryotic and prokaryotic organisms, and parasitic organisms. In a preferred embodiment, the virus is selected from Influenza virus, Flavivirus, Paramyxovirus, Hepatitis virus, human immunodeficiency virus, and viruses causing hemorrhagic fever. In another preferred embodiment, the infectious agent is *bacillus anthracis*.

In one embodiment, the immunogenic composition is administered between 24 hours prior to infection with the infectious agent and 24 hours after infection with the infectious agent. The immunogenic composition can be administered at the same time as infection with the infectious agent. The administration to the animal of the immunogenic composition comprising an MVA can be between 0 and 24 hours prior to infection with an infectious agent or between 0 and 48 hours after infection with an infectious agent.

The invention also encompasses a kit for inducing an immune response against an infectious agent in an animal, including a human, comprising an immunogenic composition comprising a poxvirus as active substance, wherein said poxvirus is replication incompetent in said animal, including a human.

Preferably, said kit comprises an immunogenic composition comprising an MVA, and instructions to deliver the immunogenic composition at a time point between 0 hours and 36 hours prior to exposure to an infectious agent or at a time point between 0 hours and 72 hours after exposure to an infectious agent. In one embodiment, the MVA is MVA-BN® at dose of $10^5$ to $5\times10^8$ TCID50.

In one embodiment, the infectious agent is smallpox. In another embodiment, the infectious agent is *bacillus anthracis*. The infectious agent may also be comprised within the kit in a separate vial.

In a preferred embodiment, the invention encompasses a kit comprising an immunogenic composition comprising an MVA and instructions to deliver the immunogenic composition as soon as possible after exposure to smallpox.

It is to be understood that both the foregoing general description and the following detailed description are exemplary and explanatory only and are not restrictive of the invention, as claimed.

BRIEF DESCRIPTION OF THE DRAWINGS

The invention is more completely understood with reference to the drawings, in which:

FIG. 4 depicts that MVA protects wild type mice if given simultaneously with lethal doses of ECTV. Wild type mice were i.n. infected with lethal doses of ECTV as indicated and simultaneously i.n. inoculated with (black symbols) or without (grey square) 1E+08 TCID50 of MVA and survival was monitored for 4 weeks. The experiments were performed with the numbers of mice as indicated and data represent the results of two individual experiments.

FIG. 5 depicts that MVA protects TLR9 deficient mice if given simultaneously with lethal doses of ECTV. TLR9-deficient mice were i.n. infected with lethal doses of ECTV as indicated and simultaneously i.n. inoculated with (black symbols) or without (grey square) 1E+08 TCID50 of MVA and survival was monitored for 4 weeks. The experiment was performed with the numbers of mice as indicated.

Figure 6:
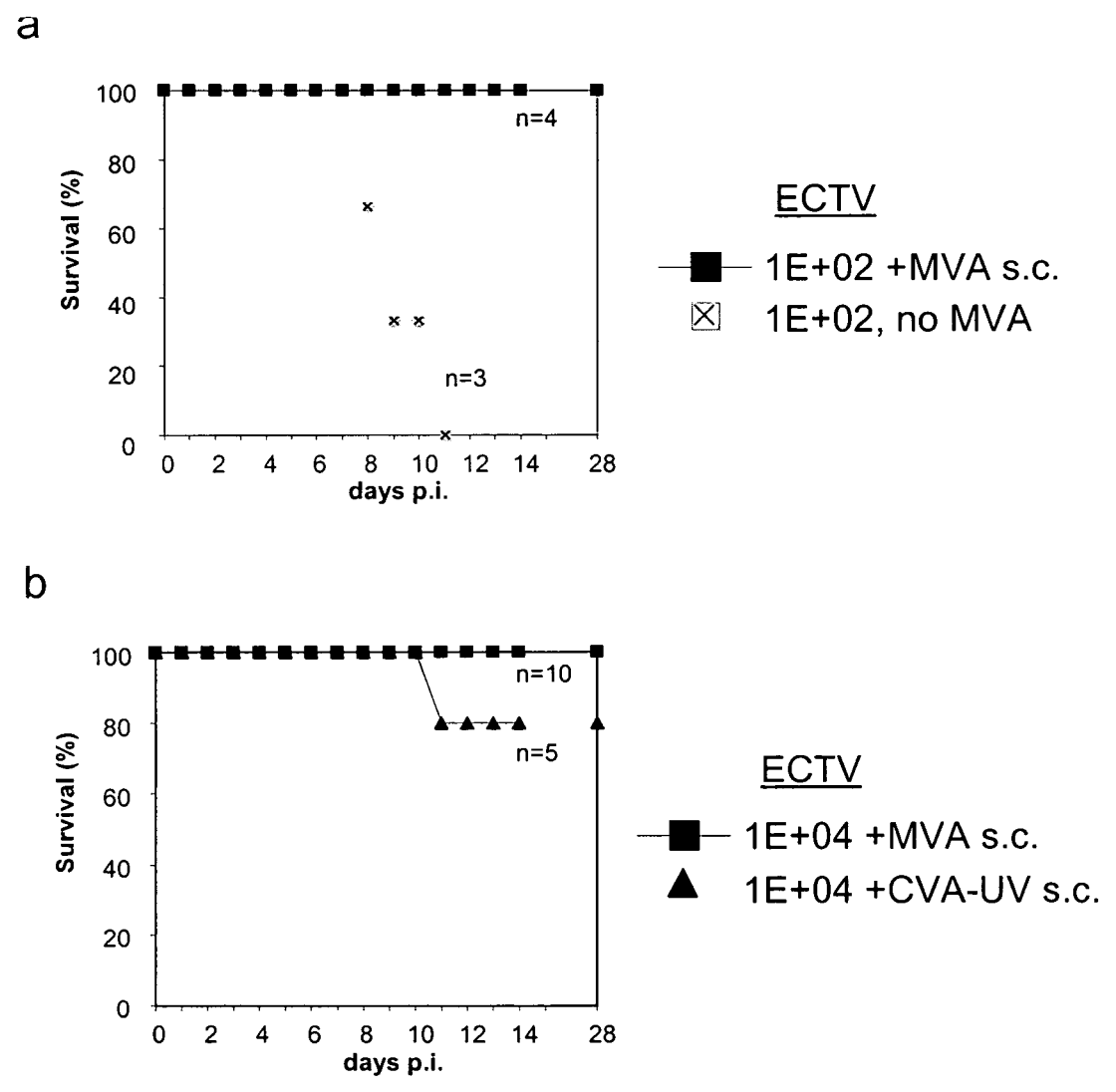

FIGS. 6a and b depict that MVA protects TLR9 deficient and wild type mice against lethal ECTV challenge if applied subcutaneously. a) TLR9 deficient mice were i.n. infected with 1E+02 TCID50 of ECTV and simultaneously s.c. inoculated with 1E+08 TCID50 of MVA (black squares) or without (grey square). b) Wild type mice were i.n. infected with 1E+04 TCID50 of ECTV and simultaneously s.c. inoculated with 1E+08 TCID50 of MVA (black squares) or with the corresponding amount of 1E+08 TCID50 of UV-inactivated CVA (black triangle). Survival was monitored for 4 weeks. The experiments were performed with the numbers of mice as indicated and data represent the results of two individual experiments for wild type mice with MVA and one experiment for wild type mice with UV-inactivated CVA or for TLR9 deficient mice with MVA.

DETAILED DESCRIPTION OF THE INVENTION

Figure 1:
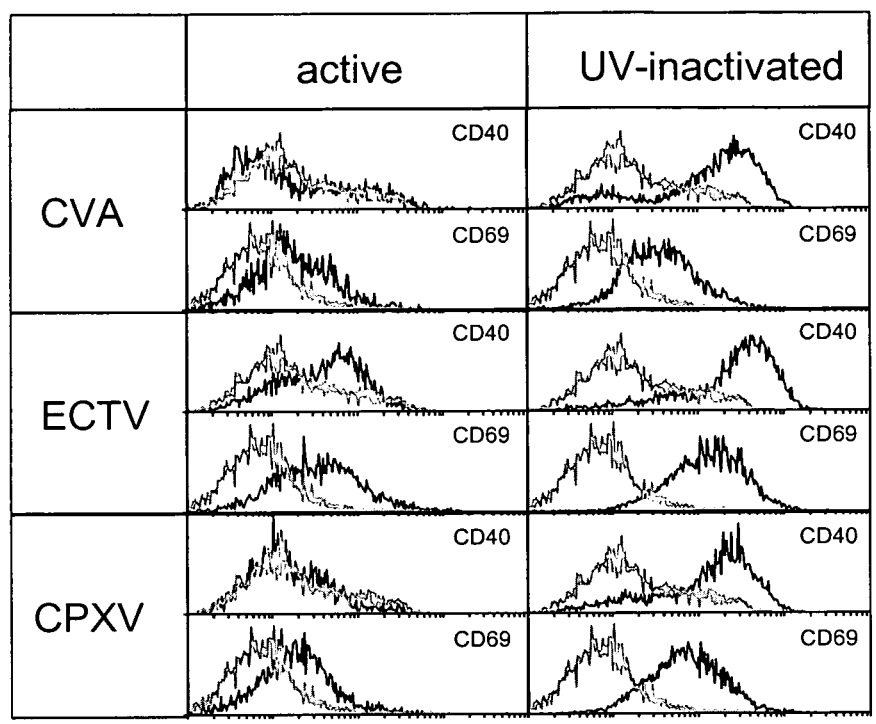
FIGS. 1a and b depict analysis of Dendritic cell (DC) maturation in response to active or inactivated poxviruses. Flow cytometry histograms showing expression of CD40 or CD69 on FL-DC after incubation with active (left panel) or inactive (right panel) poxviruses (shaded histograms) as indicated. a) CVA, ECTV, CPXV. b) MVA, SFV, CNPV or without stimulation (empty histograms). One representative experiment of at least three (CVA, ECTV, MVA) or two (CPXV, SFV, CNPV) experiments is shown.
Figure 1:
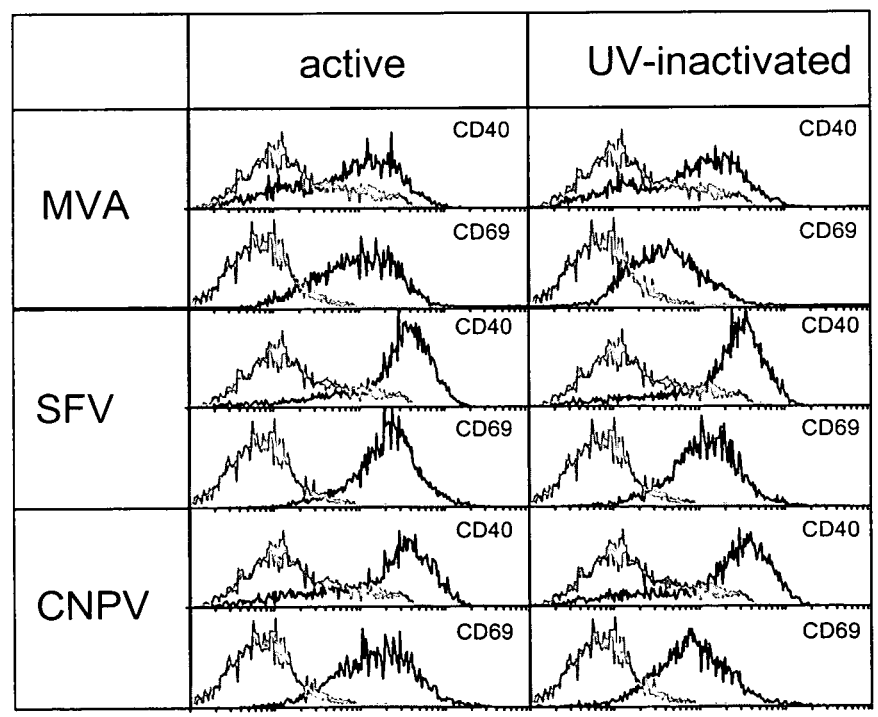

Reference will now be made in detail to the present embodiments (exemplary embodiments) of the invention, examples of which are illustrated in the accompanying drawings and Examples section.

An animal model applying intranasaly the species specific and highly pathogenic mousepoxvirus Ectromelia was used. Like Variola, which is highly specific for the human species, Ectromelia is highly specific for mice. Both Ectromelia and Variola employ a large panel of immune-suppressive strategies and, when compared to other pathogenic poxviruses e.g. "Vaccinia virus Western Reserve", they are evolutionarily more distant to MVA. Furthermore, both viruses are highly pathogenic (low virus numbers are able to establish infection and cause death in many of the infected individuals) in their specific hosts. Importantly, both Variola and Ectromelia, are able to infect their hosts via the respiratory route as a natural way of infection. For these reasons, Ectromelia infection in mice is a good model system for infection of humans by Variola.

The experiments in animals demonstrate that the co-administration of MVA together with a highly lethal dose of mousepoxvirus protects mice immediately against the deadly exposure. Immune competent mice survived the infection under these conditions when exposed to at least 47 fold the lethal dose of Ectromelia.

In addition, immune compromised mice were employed in the Ectromelia infection model. In one model, the mice lack the antiviral receptor TLR9 (TLR9-KO). The pDC of the TLR9-KO mice can not respond in the usual anti-viral way to DNA and DNA viruses. It was found that these mice have a drastic increase in susceptibility to Ectromelia infection (more than 100-fold more susceptible than immune competent mice).

With research in vitro with isolated cells, it was found that MVA is not as dependent on this specialized anti-viral pDC. The data described herein showed that MVA can employ additional immune stimulatory pathways that result in the induction of antiviral mechanisms. Thus, it was analyzed whether that MVA would also be able to protect TLR9-KO mice via the alternative pathways that were found in vitro. Indeed, application of MVA at the same time as a highly deadly dose of Ectromelia protected TLR9-KO mice immediately against at least 500-fold the lethal dose of Ectromelia.

Another immune compromised mouse model was tested that lacks responsiveness to type I interferons (IFN-I). These cytokines are believed to be essential for survival of viral infection in general. Unexpectedly, application of MVA at the time of infection with a deadly dose of Ectromelia showed some protection. Thus, this invention protects normal as well as several immune compromised individuals against otherwise deadly pathogens.

In contrast to prior studies, the data described herein with Ectromelia show that immediate protection can be achieved (giving protecting MVA at the same time as, or after, the pathogenic poxvirus). The level of protection is not only reached much earlier (at the same time/after vs. at the latest 2 days before), but is also much more effective. In immune competent mice, the protection factor exceeds 47×LD50. Furthermore, it is demonstrated that the protection in immune compromised mice exceeds the factor of 500×LD50. Ectromelia infection in mice is the best infection model currently available for correlations to Variola infections in humans.

It is shown here that poxviruses are recognized via TLR9 dependent and independent recognition pathways. Herein, it is demonstrated that pathogenic poxviruses like Ectromelia virus effectively suppress the recognition via the TLR9 independent pathway but are still recognized to some extent via TLR9.

Plasmacytoid DC (pDC) are the only cells which produce large amounts of the antiviral and immune regulating cytokines Type I Interferons (IFN-I) via TLR9 (recognizing pathogenic DNA), whereas other cells are able to produce low levels of IFN-I via different pathways, independent of TLR9.

Herein, it is described that some pathogenic poxviruses like Ectromelia virus completely abolish the TLR9 independent IFN-I production of fibroblasts and conventional cDC, whereas the TLR9 driven IFN-I production of pDC is only reduced but not prevented. In vivo infection studies with the mouse specific poxvirus Ectromelia revealed that mice lacking TLR9 have a more than 100-fold increase in susceptibility. A similar susceptibility and death kinetic in mice unable to respond to IFN-I was not found, which is known to be essential for fighting viral infection. It is concluded that, under conditions where pathogenic viruses effectively inhibit the TLR9 independent recognition, the importance of TLR9 dependent viral recognition and IFN-I production becomes essential. Thus, it is herein demonstrated that TLR9 is an important, and in vivo highly relevant, PRR for the defense against poxviruses.

MVA-BN®, a highly attenuated poxvirus that has lost the ability to replicate in mammals, is a potent inducer of robust adaptive immune responses, and vaccinated individuals are protected against species specific poxviruses (e.g. Mousepox, monkeypox, Vaccinia). However, effective induction of adaptive immune responses takes several days to weeks, which leaves individuals unprotected against exposure to these pathogens during that time. It is shown herein that MVA-BN® induces the production of innate immune-protecting cytokines (e.g. IFN-I), importantly via both TLR9 dependent and independent pathways. This production of innate immune-protecting cytokines by MVA is an unspecific immune response, which can be employed in strategies to protect against a multitude of pathogens.

Co-administration of MVA-BN® together with the highly pathogenic mousepoxvirus Ectromelia protected immune competent mice against doses of Ectromelia at least 47-fold the lethal dose. In the absence of TLR9, MVA induced immediate protection to doses of Ectromelia at least 500-fold the lethal dose. Experiments further demonstrate that even mice that lack responsiveness to IFN-I can be protected via MVA administration. Since MVA protects, if applied at the same time as, or after, the pathogenic poxvirus, the results described herein show an immediate protection, which is much earlier but in addition much more pronounced (>500× LD50) than previous data showing that MVA has to be applied at the latest 2 days before the exposure to the pathogenic virus to gain some survival benefit (1×LD50) (WO2006/089690 and Staib et al. 2006, *J. Gen. Virol.* 87:2917-2921 (2006)).

Administration of MVA around the time of lethal Ectromelia infection led to a solid immediate protection against death in immune competent and TLR9 deficient mice. This immediate protection was only partially dependent on a functional IFN-I pathway but fully dependent on adaptive immune responses, as shown with IFN-I-Receptor and Rag-1 deficient mice respectively. Importantly, MVA also rescued TLR9 deficient mice if administered two full days after an otherwise lethal infection with Ectromelia virus. Thus, MVA induced a solid immediate and even post-exposure protection against lethal poxvirus infection in immune-competent as well as immune-compromised animals.

MVA not only protects immediately, but the induced protection is, in addition, long lasting. Mice lacking TLR9 (LD50=19) treated with only 1 application of MVA were protected when challenged after 9 weeks with high lethal doses of Ectromelia (>500×LD50).

MVA-BN® not only induces strong adaptive immune responses (for example high titers of neutralizing antibodies), but in addition induces strong innate immune responses via cells including dendritic cells, that produce IFN-I which leads to a highly effective and, importantly, immediate protection against challenge with lethal poxvirus. Thus, MVA-BN® bridges innate and adaptive immune responses which results in immediate and long lasting protection to lethal poxvirus challenge. This protection can be extended to other pathogens by using a recombinant MVA expressing antigenic epitopes of the pathogens.

In these studies, MVA not only protected if given around the time of infection, but application as late as 2 days fully and 3 days partially protected mice from lethal ECTV infection. Prior scientific evidence for post-exposure vaccination in orthopoxvirus-naïve individuals is lacking (Mortimer, P. P. 2003. Can postexposure vaccination against smallpox succeed? Clin. Infect. Dis. 36:622-629). The statements of official Health sites, e.g. WHO, of the potential success of post-infection vaccinations most likely were with regard to individuals who had previously been vaccinated against smallpox, thus referring to boost vaccination which most likely quickly enhanced existing adaptive memory responses. However, after the successful eradication of variola as a natural pathogen in the 1980's, widespread vaccinations were halted and now the majority of the world population has never been vaccinated before. Moreover, the prior studies were performed on patients who were vaccinated with a fully replication competent poxvirus, not MVA.

Animal models using either VACV-WR in mice or MPXV in monkeys have not shown therapeutic protection (Stittelaar et al., *J. Virol.* 79:7845-7851 (2005); Staib et al., *J. Gen. Virol.* 87:2917-2921 (2006)).

Several reasons could explain the differences between the described models and the present findings. Both VACV-WR in mice and MPXV in monkeys are regarded as models reflecting only a late stage of smallpox infection due to the non-physiologically high doses which need to be applied for a lethal infection of the respective model animals. However, ECTV lethal infections in mice can be induced with low virus doses via the respiratory route, more resembling the beginning of a natural smallpox infection. Furthermore, VACV-WR induces pathologies in mice such as high neurovirulence, drastic drop of body weight and temperature, features not typical of ECTV in mice or VARV infections in humans. This and possibly other reasons lead to a very rapid death of the infected animals, again not seen in the ECTV model or during natural smallpox infection.

In the case of the MPXV challenge in monkeys, therapeutic vaccination was done with VACV-Elstree. It was tested whether VACV-Elstree would be inhibitory and it was found that DC maturation and cytokine production in vitro was inhibited as seen with other VACV strains. Given that therapeutic protection presumably needs a solid induction of innate immune mechanisms including antiviral cytokines to bridge the time for the adaptive immune responses to develop, therapeutic application of a non inhibitory orthopoxvirus like MVA might be also beneficial in monkeys infected with MPXV. Indeed, Staib and colleagues (2006) have shown that mice were better protected with MVA than with VACV-Elstree if applied latest 2 days before challenge with VACV-WR (Staib et al., *J. Gen. Virol.* 87:2917-2921 (2006)). Thus, MVA seems to display protective advantages over VACV-Elstree in pathogenic orthopoxvirus infection models where the induction of innate immune mechanisms plays an important role.

The invention induces robust and, most importantly, immediate protection to a very high dose of exposure with a species-specific poxvirus in normal as well as immune compromised individuals. Moreover, this protection is long lasting. Thus, the invention provides an ideal treatment under conditions where quick protection against deadly poxvirus infections is needed (e.g. terroristic or accidental exposure to smallpox or other pathogenic poxviruses).

The invention also encompasses the use of MVA and recombinant MVA as emergency tools against a large panel of other pathogens. The invention further encompasses other attenuated viruses and bacteria as emergency tools against a large panel of pathogens. In addition, the invention could be employed for therapeutic intervention, giving the emergency tools, e.g. MVA, after exposure to the pathogen, e.g., smallpox.

The invention encompasses the use of a poxvirus for the preparation of a vaccine for the rapid induction of a protective immune response in an animal, including a human, wherein the poxvirus is replication incompetent in the animal, including in the human.

The invention also encompasses a vaccine comprising a poxvirus for the rapid induction of a protective immune response in an animal, including a human, wherein the poxvirus is replication incompetent in the animal, including in the human.

In one embodiment, the invention encompasses a method for the rapid induction of a protective immune response in an animal, including a human, comprising the step of administering to the animal, including the human, a poxvirus that is replication incompetent in the animal, including in the human.

The term "replication incompetent" means that the virus shows an amplification ratio of less than 1 in human cell lines, such as the cell lines 293 (ECACC No. 85120602), 143B (ECACC No. 91112502), HeLa (ATCC No. CCL-2) and HaCat (Boukamp et al., *J. Cell Biol.* 106(3): 761-71 (1988)), under the conditions as outlined in Example 1 of WO 02/42480 for some specific MVA strains and that the virus does not replicate in humans and in the mice model as described in the WO 02/42480 publication.

In one embodiment, the invention encompasses a use, vaccine or method as above, wherein the protective immune response is generated in less than 2 days.

In one embodiment, the poxvirus is a Modified Vaccinia virus Ankara (MVA), particularly MVA 575, MVA 572 and, preferably, MVA-BN®.

The invention also encompasses uses, vaccines or methods as above, wherein the virus is a cloned, purified virus. Particularly, the invention encompasses viruses obtained in a serum free cultivation process.

In one embodiment, the poxvirus is administered in a dose of $10^5$ to $5 \times 10^8$ TCID$_{50}$. The poxvirus, in particular MVA can be administered, for example by oral, nasal, intramuscular, intravenous, intraperitoneal, intradermal, intra-utero and/or subcutaneous application. In small animals the inoculation for immunization is preferably performed parenterally or nasally, whereas in larger animals or humans a subcutaneous, intramuscular or oral inoculation is preferred.

In the context of the present invention the term "animal" covers also human beings. More generally, the animal is a vertebrate animal, preferably a mammalian animal including a human. Specific examples for animals are pets such as dogs, cats, economically important animals such as calves, cattle, sheep, goats, horses, pigs and other animal such as mice, rats. The invention may also be used for economically important birds such as turkeys, ducks, goose and hens if viruses are used that are capable to infect the bird's cells but not capable of being replicated to infectious progeny virus in said cells.

The term "domestic animals" as used in the present description refers preferably to mammalian domestic animals, more preferably to dogs, cats, calves, cattle, sheep, goat, pigs, horses, deers.

Preferably, the immune response is a protective immune response against a poxvirus infection, preferably, a smallpox infection. The protective immune response can preferably protect against a dose of 1, 5, 10, 25, 50, 100, 250, or 500 LD 50 of smallpox.

In one embodiment, the poxvirus is a recombinant poxvirus, preferably a recombinant MVA-BN®.

The poxvirus can comprise at least one heterologous nucleic acid sequence. The term "heterologous" as used in the present application refers to any combination of nucleic acid sequences that is not normally found intimately associated with the virus in nature, Preferably, the heterologous nucleic acid sequence is a sequence coding for at least one antigen, antigenic epitope, and/or a therapeutic compound. A "therapeutic compound" encoded by the heterologous nucleic acid in the recombinant virus can be, e.g., a therapeutic nucleic acid such as an antisense nucleic acid or a peptide or protein with desired biological activity. The antigenic epitopes and/or the antigens can be antigenic epitopes and/or antigens of an infectious agent. The infectious agents can be viruses, fungi, pathogenic unicellular eukaryotic or prokaryotic organisms, and parasitic organisms. The viruses can be selected from the family of Influenza virus, Flavivirus, Paramyxovirus, Hepatitis virus, Human immunodeficiency virus, or from viruses causing hemorrhagic fever. The infectious agent can be *bacillus anthracis*.

The insertion of heterologous nucleic acid sequences is preferably into a non-essential region of the virus genome. Alternatively, the heterologous nucleic acid sequence is inserted at a naturally occurring deletion site of the viral genome (for MVA disclosed in PCT/EP96/02926). Methods how to insert heterologous sequences into the viral genome such as a poxviral genome are known to a person skilled in the art.

According to a further embodiment the invention concerns the recombinant poxvirus according to the present invention for use as vaccine or medicament.

In one embodiment, the MVA virus is a strain characterized by having at least one, two, or preferably three of the following advantageous properties:
(i) capability of reproductive replication in vitro in chicken embryo fibroblasts (CEF), but no capability of reproductive replication in a human cell line, as in the human keratinocyte cell line HaCaT, the human embryo kidney cell line 293, the human bone osteosarcoma cell line 143B, and the human cervix adenocarcinoma cell line HeLa;
(ii) failure to replicate in a mouse model that is incapable of producing mature B and T cells and as such is severely immune compromised and highly susceptible to a replicating virus; and
(iii) induction of at least the same level of specific immune response in vaccinia virus prime/vaccinia virus boost regimes when compared to DNA-prime/vaccinia virus boost regimes.

For the preparation of immunogenic compositions, the MVA vaccinia viruses according to the invention are converted into a physiologically acceptable form. This can be done based on the experience in the preparation of MVA vaccines used for vaccination against smallpox (as described by Stickl, H. et al., *Dtsch. med. Wschr.* 99:2386-2392 (1974)). Typically, about $10^6$-$10^8$ particles of the recombinant MVA are freeze-dried in phosphate-buffered saline (PBS) in the presence of 2% peptone and 1% human albumin in an ampoule, preferably a glass ampoule. The lyophilisate can contain extenders (such as mannitol, dextran, sugar, glycine, lactose or polyvinylpyrrolidone) or other aids (such as antioxidants, stabilizers, etc.) suitable for parenteral administration. The glass ampoule is then sealed and can be stored, preferably at temperatures below −20° C., for several months.

For administration or therapy the lyophilisate can be dissolved in 0.1 to 0.5 ml of an aqueous solution, preferably physiological saline, and administered either parenterally, for example by intramuscular inoculation. Immunogenic compositions, vaccines or therapeutics according to the invention are preferably injected intramuscularly (Mayr, A. et al., *Zbl. Bakt. Hyg., I. Abt. Orig. B* 167:375-390 (1978)). The mode of administration, the dose and the number of administrations can be optimized by those skilled in the art in a known manner. It is expedient, where appropriate, to administer the immunogenic compositions, vaccines or therapeutics one time, or several times over a variable period in order to obtain appropriate immune responses against the foreign antigen.

In one embodiment, the poxvirus is an inactivated orthopoxvirus. Preferably, the orthopoxvirus is inactivated with UV radiation. In preferred embodiments, the orthopoxvirus is CVA, ECTV, or CPXV.

It is an object of the present invention to provide a method for vaccinating an individual against a pathogen so as to provide immediate protection. In one embodiment, the individual is vaccinated with MVA, preferably MVA-BN®, near the time of pathogenic exposure. Preferably, the vaccination is between 2 days prior to exposure and 3 days post-exposure. More preferably, the vaccination is between 2 days prior to the exposure and 1 day post-exposure. Even more preferably, the vaccination is between 1 day prior to the exposure and 1 day post-exposure. The vaccination can be at 2 days prior, 36 hours prior, 1 day prior, 12-24 hours prior, or 0-12 hours prior to the exposure. The vaccination can also be at the time of the exposure or 0-12 hours post-exposure, 12-24 hours post-exposure, 1 day post-exposure, 2 days post-exposure, 0-36 hours post-exposure, 0-48 hours post-exposure, 0-60 hours post-exposure, 0-72 hours post-exposure, 3 days post-exposure, 4 days post-exposure, or even 10 days post-exposure.

The invention includes a method for inducing a immune response against an infectious agent in an animal comprising administering to the animal an immunogenic composition comprising an MVA, preferably MVA-BN®, at 2 to 0 days, or 1 to 0 days, or any other combination of the hours comprised by these days (e.g., 48-36, 48-24, 36-24, 24-12, 12-0, etc.) prior to infection with an infectious agent. In one embodiment, the infectious agent is a replication competent poxvirus. In a preferred embodiment, the animal is a human.

The invention includes a method for inducing a immune response against an infectious agent in an animal comprising administering to the animal an immunogenic composition comprising an MVA, preferably MVA-BN®, at 0 to 3 days, 0 to 2 days, 0 to 1 days, or 1 to 2 days, or any other combination of the hours comprised by these days (e.g., 0-12, 12-24, 24-36, 24-48, 24-72, 36-48, 48-60, 48-72, etc.) after infection with an infectious agent. In one embodiment, the infectious agent is a replication competent poxvirus. In a preferred embodiment, the animal is a human.

The invention further encompasses uses of the above methods and kits comprising an immunogenic composition comprising an MVA, preferably MVA-BN®, and instructions to deliver the immunogenic composition at a time point between 2 and 0 days prior to exposure to an infectious agent, including 2, 1, or 0 days prior to exposure, as well as 36, 12, 6, 3, or 1 hour prior to exposure. The time point can be within any combination of the hours comprised by these days (e.g., 48-36, 48-24, 36-24, 24-12, 12-0, etc.) prior to infection with an infectious agent.

The invention also encompasses uses of the above methods and kits comprising an immunogenic composition comprising an MVA, preferably MVA-BN®, and instructions to deliver the immunogenic composition at a time point between 0 and 3 days after exposure to an infectious agent, including 0, 1, 2, or 3 days after exposure, as well as 1, 3, 6, 12, 36, or 60 hours after exposure. The time point can be within any combination of the hours comprised by these days (e.g., 0-12, 12-24, 24-36, 24-48, 24-72, 36-48, 48-60, 48-72, etc.) after infection with an infectious agent.

The invention also encompasses kits for the induction of a protective immune response in an animal. Preferably, said immune response is directed against an infectious agent as defined herein. In one embodiment, the kit comprises an immunogenic composition comprising a poxvirus, wherein said poxvirus is replication incompetent in said animal. In a preferred embodiment, said poxvirus is a Modified Vaccinia Virus Ankara (MVA). The kit may also comprise instructions for the delivery of the immunogenic composition. The MVA is preferably MVA-BN. Preferably, the immunogenic composition contains $10^5$ to $5 \times 10^8$ TCID$_{50}$/ml of MVA. In a preferred embodiment, the animal is a human. The instructions for delivery of the immunogenic composition can direct the delivery at various time points prior to exposure or after exposure to an infectious agent. These time points can include time points between 2 days prior to exposure to an infectious agent and 3 days after exposure to the infectious agent. In one embodiment, the instructions direct that the MVA is delivered after exposure to the infectious agent, preferably as soon as possible after exposure to the infectious agent, which is preferably smallpox. The kit may further comprise an infectious agent as defined herein in a separate vial and instructions for the delivery of the infectious agent to an animal, including a human. The infectious agent is preferably selected from *bacillus anthracis* or smallpox.

In this context, an "exposure" means contact with the infectious agent itself, or with an animal (human) harboring the infectious agent. For example, the instructions can direct that the immunogenic composition can be delivered at 36, 24, 12, 6, 3, or 1 to 0 hours prior to exposure to an infectious agent or at 0 to 1, 3, 6, 12, 24, 36, 48, 60, or 72 hours after exposure to an infectious agent. For example, the instructions can direct delivery at 48-36, 48-24, 36-24, 24-12, 12-0, etc., prior to infection with an infectious agent or 0-12, 12-24, 24-36, 24-48, 24-72, 36-48, 48-60, 48-72, etc. after infection with an infectious agent. Preferably, the infectious agent is smallpox or *bacillus anthracis*. The instructions can direct that the MVA be administered intravenously, intramuscularly, and/or subcutaneously. The instructions can direct that the MVA be administered intranasally.

The pathogen is preferably a virus or a bacterium. In a preferred embodiment, the pathogen is a poxvirus, preferably a Variola virus.

In one embodiment, the individual is a healthy human. In another embodiment, the individual is an immunocompromised human, for example, an HIV-1 infected individual, an individual with atopic dermatitis, a patient taking immunosuppressive drugs, or an individual with allergies.

Modified vaccinia virus Ankara (MVA), a host range restricted and highly attenuated vaccinia virus strain, is unable to multiply in human and other mammals tested. But, since viral gene expression is unimpaired in non-permissive cells, the recombinant MVA viruses according to the invention may be used as exceptionally safe and efficient expression vectors.

Poxviruses including the causative agent of smallpox, variola virus, have developed multiple strategies to suppress immune responses. The invention provides evidence that poxviruses are recognized via toll-like receptor (TLR)9-dependent as well as TLR9-independent pathways. Pathogenic poxviruses effectively suppressed their recognition via the TLR9-independent pathway employed by conventional dendritic cells (DC), but were detected by plasmacytoid DC (pDC) via TLR9. The lack of TLR9 abrogated the DC response in vitro and drastically increased the susceptibility of mice to infection with the murine poxvirus Ectromelia virus (ECTV). Simultaneous administration of modified vaccinia virus Ankara (MVA)-BN® at the time of infection led to a solid immediate protection against ECTV, even in the absence of TLR9 or interferon type I receptor (IFN-I-R). MVA-BN® also rescued mice if administered after infection with ECTV. Thus, MVA-BN® induced a solid immediate and even post-exposure protection against lethal ECTV infection in immune-competent as well as immune-compromised mice.

The data presented below in Examples 1 through 11 demonstrate that poxviruses, as shown previously for other families of dsDNA viruses, are detected via TLR9-dependent as well as TLR9-independent recognition pathways. MVA, a highly attenuated VACV that has lost its capacity to replicate in human cells, was found to be recognized by pDC via both TLR9-dependent and TLR9-independent pathways, whereas in cDC it was only recognized via the TLR9-independent pathway. This finding is consistent with previous findings with HSV-1 (Hochrein, H. et al., *Proc. Natl. Acad. Sci. U.S.A* 101, 11416-11421 (2004)). However, in sharp contrast, the recognition of the pathogenic poxviruses, including several strains of VACV, ECTV or CPXV critically relied on TLR9 and pDC, likely due to the potent ability of these viruses to inhibit their recognition via TLR9-independent pathways. In the absence of pDC or TLR9, this inhibitory potential nearly completely abrogated immune recognition and thus response by DC in vitro. This translated into the in vivo infection model with ECTV, where TLR9 deficient mice were more than 100-fold more susceptible than wild type mice.

Since the response to the inactivated VACV, CPXV and ECTV viruses depended on the presence of TLR9, these viruses most likely inhibit both the TLR9-dependent and the TLR9-independent activation pathways. Strikingly, in the absence of TLR9, this inhibition was virtually absolute as even the most sensitive readout of DC maturation (CD69 expression) was abolished. Several poxvirus encoded inhibitory genes including the VACV product of A46R and A52R (Bowie et al., *Proc. Natl. Acad. Sci. U.S.A.* 97:10162-10167 (2000); Harte et al., *J. Exp. Med.* 197:343-351 (2003); Stack et al., *J. Exp. Med.* 201:1007-1018 (2005)) have been implicated in the inhibition of TLR signaling molecules. Genetic comparisons of ECTV, CVA, CPXV and MVA show that all 4 viruses have homologues of A46R (Meisinger-Henschel et al., *J. Gen. Virol.* 88:3249-3259 (2007)). CVA and CPXV also express homologues of A52R whereas MVA lacks this component. ECTV strain Moscow which we have used for this study has a fragmented A52R gene which most likely is not functional (Chen et al., *Virology* 317:165-186 (2003)). To elucidate the potential role of A46R and A52R in the inhibition of DC activation via the TLR9 dependent and independent recognition pathways, recombinant VACVs lacking or expressing A46R and A52R have been constructed. A recombinant MVA expressing A52R as well as endogenous A46R, thus resembling the inhibitory CVA (endogenously expressing A46R and A52R), did not demonstrate any significant increased inhibition compared to wild type MVA as judged by analyses of DC maturation and cytokine induction. In contrast, a deletion mutant of CVA expressing neither A46R nor A52R did not lose its inhibitory potential. This is in accordance with previously published data showing that an A52R defective VACV still retained inhibitory activity against DC maturation (Drillien et al, *J. Gen. Virol.* 85:2167-2175 (2004)). Taken together, these data suggest that neither A46R (endogenously expressed by the non inhibitory MVA) nor A52R are the major inhibitory component of the TLR9-dependent or TLR9-independent recognition defined within this study.

The nature of TLR9-independent recognition in response to MVA is still elusive as are the recognition pathways in response to other DNA viruses (Ishii et al., *Trends Immunol* 27:525-532 (2006)). However, recent reports rule out the absolute dependence on the presence of the TLR associated adaptor molecules MyD88 and TRIF as well as PKR (Zhu et al., *Blood* 109:619-625 (2007); Waible et al., *J. Virol.* 81:12102-12110 (2007),). Recently a new intracellular sensor for DNA (DAI) was identified (Takaoka et al., *Nature* 448:501-505 (2007)). Infecting cells in the presence or absence of a siRNA silencing DAI indicated that the response to transfected DNA or HSV-1 but not to RNA was to some extent dependent on DAI. However, the response to HSV-1 was reduced but not abrogated (responses to poxviruses were not tested) suggesting the existence of additional DNA virus recognition pathways. Others have shown that mouse embryonic fibroblasts responded to MVA (lacking the gene E3L) independently of the presence of the noncanonical IκB kinase family members TBK1 and IKKi (Ishii et al., *Nat. Immunol.* 7:40-48 (2006)) and that the induction of IFN-α in response to MVA was independent of virus propagation and DNA replication (Waible et al., *J. Virol.* 81:12102-12110 (2007)).

In the case of TLR9-independent recognition of HSV, recent publications suggest that different cell types might have different requirement. In cDC, the IFN response was independent of viral replication but dependent on viral entry. In contrast, in macrophages and fibroblasts, IFN-I production was dependent on both viral entry and replication and in addition on a functional mitochondrial signaling protein pathway, which suggest a possible involvement of RNA components (Rasmussen et al., *J. Virol.* 81:13315-13324 (2007); Weber et al., *J. Virol.* 80:5059-5064 (2006)). Thus, the immunological recognition of DNA viruses seems at least as redundant as the recognition of RNA viruses. Suppressive mechanisms developed by different viruses, some of those employed by poxviruses, most likely put an enormous evolutionary pressure on the development of redundant DNA virus recognition pathways.

Poxviruses are divided into two subfamilies, the poxviruses infecting invertebrates e.g. insects (entomopoxvirinae) and poxviruses infecting vertebrates (chordopoxvirinae). Many, if not all species of vertebrates, have battled throughout evolution for their survival against highly pathogenic poxviruses. Today, poxviruses infecting reptiles, birds and many different species of mammals are known. Vertebrates as early as fishes are known to respond to CpG-DNA stimulation suggesting the expression of TLR9. One could speculate that the TLR9 system, as well as the specialized DC subset employing TLR9 for IFN-I production, pDC, were optimized under strong evolutionary pressure for the detection of and the defense against poxviral infections.

TLR9 expression in murine and human cells differs greatly. Whereas in both species pDC and B-cells are positive for TLR9 and respond to TLR9 stimulation, murine cDC subsets and macrophages also express TLR9. Moreover, different cell types even within one species respond differentially and selectively to TLR9 ligands. This includes not only the unique IFN-α producing capacity of pDC but is also demonstrated in selective responses of B-cells to different TLR9 agonists. Previously, it was described that murine B-cells are activated and proliferate to a B-type CpG-ODN but not to an A-Type CpG-ODN or to purified plasmid DNA (Spies et al., *J. Immunol.* 171:5908-5912 (2003)). One possible explanation could be cell type specific uptake and endosomal processing of different TLR9 ligands. This could also possibly explain why the cDC employed in this study only displayed the TLR9-independent, but not any TLR9-dependent stimulation in response to MVA, even though they express TLR9 and respond to the artificial TLR9 agonist CpG-ODN.

The immune protection induced by MVA was clearly relevant in a setting lacking TLR9 responses and thus immune activation in response to MVA was not solely dependent upon TLR9 or pDC. This feature of MVA to induce pDC and IFN-I independent immune activation could be important under conditions described in humans where pDC numbers or function and thus TLR9-dependent IFN-I production are impaired. Among these are cancer and transplantation patients, people taking immune suppressive drugs and people with HIV, even under antiviral treatment ((Hashizume et al., *J. Immunol.* 174, 2396-2403 (2005); Donaghy, H. et al., *Blood* 98, 2574-2576 (2001); Chehimi, J. et al., *J. Immunol.* 168, 4796-4801 (2002); Boor, P. P. et al., *Am. J. Transplant.* 6, 2332-2341 (2006); Siegal, F. P. et al., *J. Clin. Invest* 78, 115-123 (1986)). Furthermore, some immune conditions like allergies are associated with reduced virus induced IFN-I production (Bufe et al., *Int. Arch. Allergy Immunol.* 127:82-88 (2002)). Of note, most of these conditions have been defined as contraindicated for the application of replication-competent smallpox vaccines.

Figure 7:
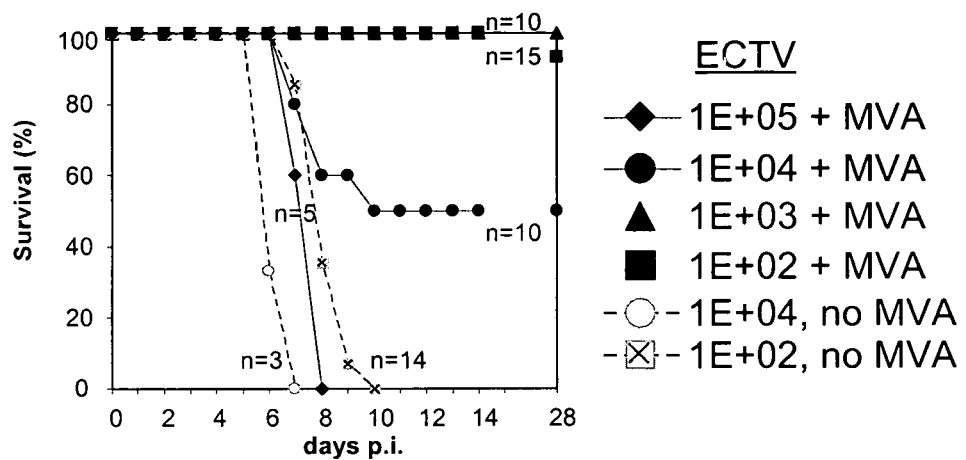
FIG. 7 depicts that MVA partially protects IFN-I-R-deficient mice if given simultaneously with lethal doses of ECTV. IFN-I-R-deficient mice were i.n. infected with lethal doses of ECTV as indicated and simultaneously i.n. inoculated with 1E+08 TCID50 of MVA (black symbols) or without (grey symbols) and survival was monitored for 4 weeks. The experiments were performed with the numbers of mice as indicated and data represent the results of at least two individual experiments for the challenge dose of (1E+02 and 1E+03) or one experiment for the challenge dose of 1E+04 and 1E+05.

Although we found that MVA was able to protect to some extent IFN-I-R deficient mice against ECTV infection (FIG. 7), application of the traditional smallpox vaccine virus, Dryvax, killed these mice even without ECTV challenge. This finding was consistent with previous reports on lethality to VACV Wyeth in other immune compromised mice (Wyatt et al., *Proc. Natl. Acad. Sci. U.S.A.* 101:4590-4595 (2004); Perera et al., *J. Virol.* 81:8774-8783 (2007)).

This study demonstrates that MVA given at the same time as lethal doses of ECTV protected wild type and TLR9 deficient mice against death (FIG. 4, FIG. 5) irrespective of the site of application, (FIG. 6), the protocol called "immediate protection." These findings indicate that MVA induces solid innate immune responses and thus bridges the time adaptive immune responses need to develop.

To define the mechanisms of the innate protection phase, the immediate protection protocol was applied to mice which lack responsiveness to IFN-I. Upon high dose exposure, these mice were not protected to the same extent as wild type mice, suggesting that IFN-I is part of the protection. However, IFN-I-R mice were protected to lower, but nevertheless lethal, doses of ECTV, clearly demonstrating that other mechanisms are able to substitute for IFN-I during the innate phase of the immediate protection protocol.

A role for TNF-α in protection against ECTV was previously shown by the increased susceptibility of TNF-Receptor deficient mice to ECTV infection as well as by the attenuation of TNF-α encoding VACV (Ruby et al., *J. Exp. Med.* 186: 1591-1596 (1997)). Using similar methods, antiviral activities were reported for IL-2, IL-6, IL-12, IFN-gamma, IFNlambda, CD40L, Mig, IP-10, NO and complement (Esteban et al., *J. Gen. Virol.* 86:2645-2659 (2005); Ramshaw et al., *Immunol. Rev.* 159:119-135 (1997); Bartlett et al., *J. Gen. Virol.* 86:1589-1596 (2005); Niemialtowski et al., *Acta Virol.* 38:299-307 (1994)). Apart from soluble components, cellular innate mechanisms like the induction of NK cells seem to play an important role during infections with poxviruses including ECTV infection (Parker et al., *J. Virol.* 81:4070-4079 (2007)). These and other mechanisms may be involved in the MVA mediated immediate protection.

Figure 8:
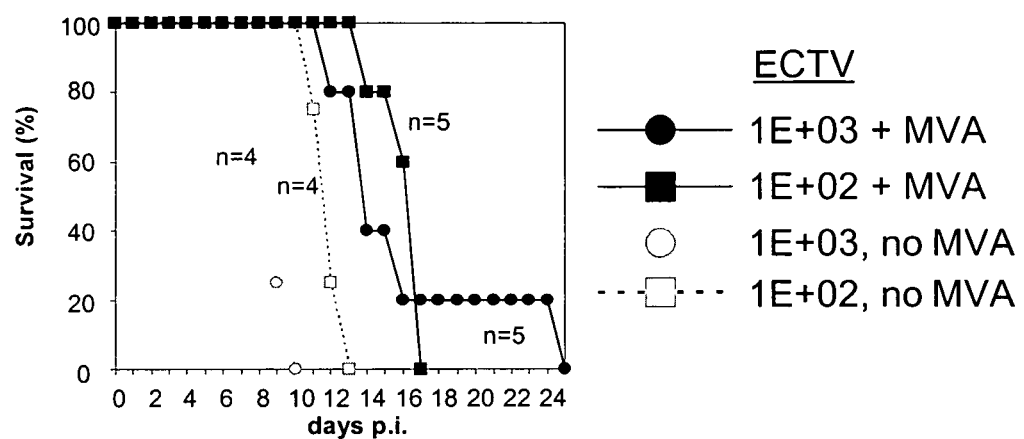
FIG. 8 depicts long time survival to ECTV infection even in the presence of MVA depends on adaptive immune responses. RAG-1 deficient mice were i.n. infected with doses of ECTV as indicated and simultaneously i.n. inoculated with 1E+08 TCID$_{50}$ of MVA (black symbols) or without (grey symbols) and survival was monitored for 4 weeks. The experiment was performed with the numbers of mice as indicated.

The failure of the immediate protection protocol to induce sustained protection in the absence of adaptive immune responses (FIG. 8) clearly indicated that survival depended ultimately on adaptive immune responses. The prolongation of survival in the RAG-1 deficient mice also gave some indication of the duration of solid protecting innate mechanisms but as described previously for traditional vaccination strategies, survival to pathogenic poxvirus infection ultimately needs adaptive mechanisms to clear the virus. This prerequisite makes it unlikely that the sole induction of innate mechanisms like application of IFN-I, TLR ligands or other non-specific innate stimuli would suffice in the protection to lethal poxvirus infection if adaptive immune responses were not effectively triggered at the same time. The experiment with UV-inactivated CVA (FIG. 6b) which carries orthopoxvirus antigens and presumably activates via TLR9 suggested that some limited protection could be achieved in immune competent mice. However, the fact that all mice at least became sick, in stark contrast to the mice treated with active MVA which stayed symptom free, indicated that the protection via the active MVA is much more solid.

TLR9 was identified as an essential and in vivo highly relevant recognition molecule for poxviruses. Importantly, it provides evidence for the use of MVA-BN® as a way for immediate and therapeutic intervention against potential fatal poxvirus infection in healthy as well as immune compromised individuals.

Here, previous data that members of the poxvirus family are recognized via TLR-independent recognition pathways (Zhu, J. et al. *Blood* 109, 619-625 (2007), are confirmed. However, it is shown that poxviruses are also seen via the TLR9-dependent pathway. It is shown that some poxviruses, like ECTV, effectively suppress the recognition via the TLR9-independent pathways but are still recognized via TLR9.

Plasmacytoid DC (pDC) are the only cells in human and mouse which produce large amounts of type I interferon (IFN-I) via the TLR9 pathway, whereas other cells including conventional DC (cDC) are able to produce IFN-I via different pathways, independent of TLR9. It is shown herein that some poxviruses completely abolish the TLR9-independent IFN-I production and affect the maturation of DC, whereas the TLR9-driven IFN-I production of pDC is not fully prevented.

In vivo studies with ECTV, a natural mouse pathogen, revealed that the lack of TLR9 renders mice more than 100 fold more susceptible to infection. A similar susceptibility and death kinetics could be found in mice unable to respond to IFN-I, which is thought to be essential to control viral infection (Muller, U. et al. Science 264, 1918-1921 (1994)). Thus, under conditions where pathogenic DNA viruses effectively inhibit their TLR9-independent recognition, the roles of TLR9-dependent viral recognition, IFN-I production and thus pDC become critical at least for primary defense mechanisms during infection.

MVA, a highly attenuated orthopoxvirus that has lost its ability to replicate in mammals, is a potent inducer of robust adaptive immune responses and vaccinated individuals are protected against other poxvirus species within the genus Orthopoxvirus (e.g. monkeypox virus (MPXV)) (Earl, P. L. et al. Nature 428, 182-185 (2004); Stittelaar, K. J. et al. J. Vir. 79, 7845-7851 (2005)). Due to an inability to replicate in mammals, MVA is tested as a vaccine candidate even in highly immune compromised individuals (Gherardi et al., *J. Gen. Virol.* 86:2925-293 6; Staib et al., *J. Gen. Virol.* 87:2917-2921 (2006)). However, effective induction of adaptive immune responses takes several days to weeks and previous reports have shown that limited survival benefits against pathogenic poxviruses can only be achieved with application of the vaccinating virus at the latest two days before exposure to the challenge virus (Staib, C. et al. J. Gen. Virol. 87, 2917-2921 (2006)).

It is shown here that MVA-BN induces the production of innate immune-protecting cytokines (e.g. IFN-I) in vitro via both TLR9-dependent and -independent pathways. Unlike poxviruses such as ECTV, MVA did not inhibit the ability of DC to recognize it via TLR9-independent pathways. This property can be useful in protection against poxviruses that displayed a more inhibitory phenotype.

Administration of MVA-BN at the same time as high doses of the highly pathogenic and species-specific mousepox virus ECTV protected not only immune-competent mice against death, but also mice which lacked TLR9 or responsiveness to type I interferon. Mice without a functional IFN-I response were protected to low and intermediate ECTV challenges however succumbed to infection if higher doses were used indicating that one mechanism of protection involves IFN-I which can be substituted to some extent by other means. However, mice lacking adaptive immune responses (Rag-1-deficient mice) had only some temporary advantage with MVA administration, but all mice died finally indicating that the induction of adaptive immune responses are essential for the overall protection to lethal poxvirus infection. Thus, MVA was capable of activating an immune response in vivo via TLR9-independent pathways, even in the presence of a poxvirus that potently inhibited this recognition. Importantly, even post-exposure application of MVA-BN protected TLR9-deficient mice from death against lethal infection by ECTV.

This study demonstrates that TLR9 is an important, and in vivo highly relevant, PRR for the recognition of, and the defense against, poxviruses. Moreover, even under conditions of compromised immune systems, MVA-BN activates and bridges innate and adaptive immune responses, resulting in long lasting but importantly also immediate and therapeutic protection against lethal poxvirus challenge.

Figure 2A:
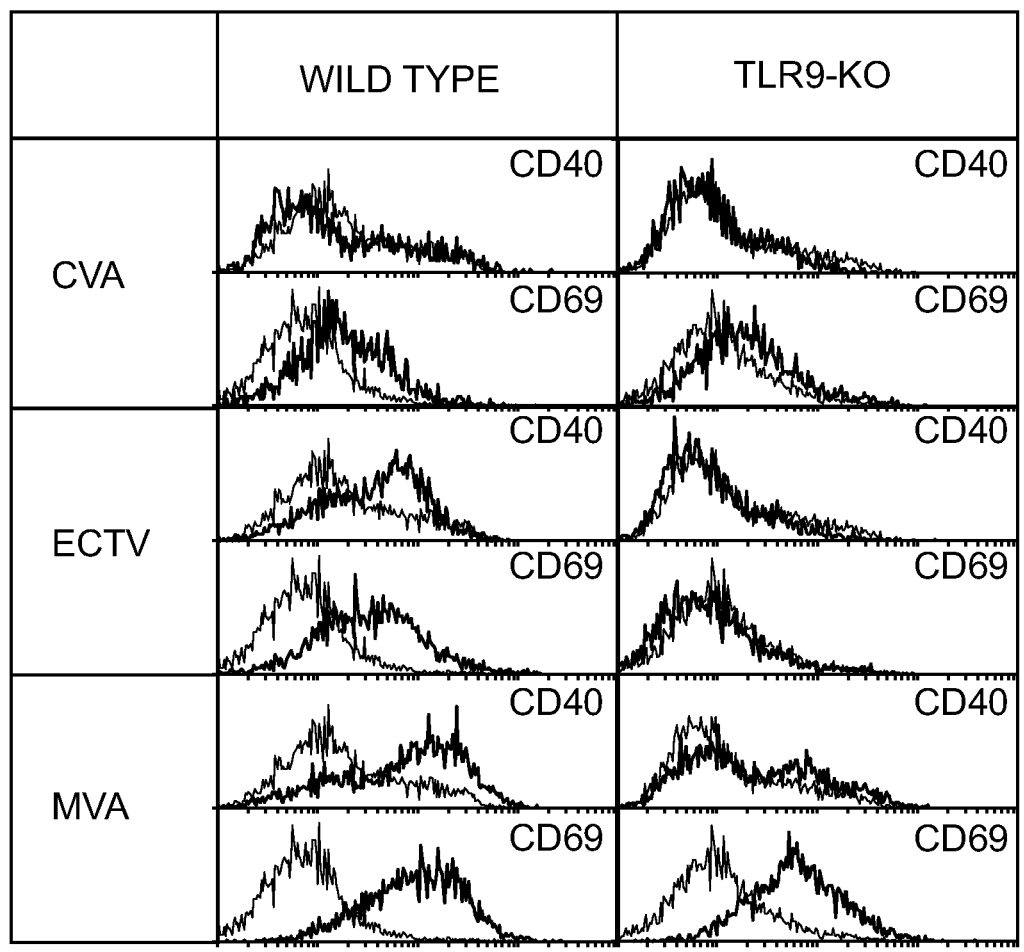
FIG. 2a-e depict response of TLR9-deficient or wild type DC to poxvirus infection in vitro. a) Flow cytometry histograms showing expression of CD40 or CD69 on FL-DC of wild type (left panel) or TLR9-deficient mice (right panel) after incubation with CVA, ECTV or MVA as indicated (shaded histograms) or without stimulation (empty histograms). The similar histograms for the wild type activation are part of FIG. 1. b) FL-DC or c) GM-DC of TLR9-deficient (empty column) or wild type mice (filled column) were stimulated with active (left panel) or UV-inactivated (right panel) MVA and the supernatants were analyzed for IFN-α and IL-6 by ELISA. d) Sorted FL-pDC and cDC of TLR9-deficient or wild type mice as indicated were stimulated with MVA (filled column) or ECTV (empty column) and supernatants were analyzed for IFN-α and IL-6 by ELISA. e) Total bone marrow cells were stimulated with active (diagonally striped column) or UV-inactivated (horizontally striped column) MVA or CpG-2216 (black column) and the supernatants were analyzed for IFN-α by ELISA. Representative experiments of at least two experiments are shown.
Figure 2B:
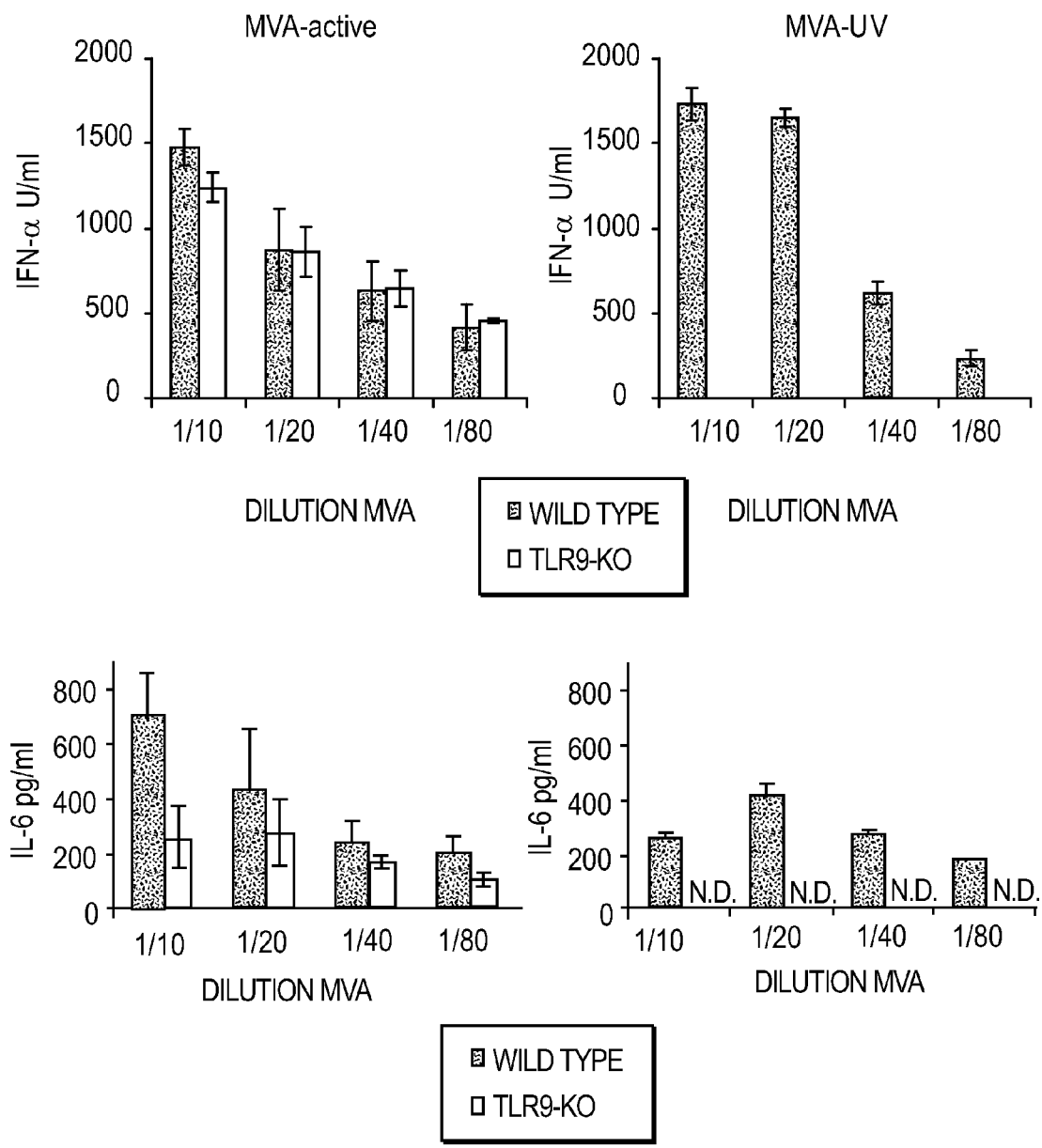

The data presented clearly demonstrate that poxviruses, as shown previously for other families of dsDNA viruses, are detected via TLR9-dependent as well as TLR9-independent recognition pathways. MVA, a highly attenuated VACV that has lost its capacity to replicate in human cells, was found to be recognized by pDC via both TLR9-dependent and TLR9-independent pathways, whereas in cDC it was only recognized via the TLR9-independent pathway. After UV-inactivation of MVA a mixed population consisting of pDC and cDC produced cytokines only in the presence of TLR9 (FIG. 2b). This finding closely resembled our previous findings with HSV-1 where active virus induced IFN-α in vitro in several DC subsets and macrophages independent of TLR9 whereas pDC employed in addition a TLR9-dependent pathway, that also recognized inactivated HSV (Hochrein et al., *Proc. Natl. Acad. Sci. U.S.A.* 101:11416-11421 (2004)). The inactivation methods employed (heat inactivation in the case of HSV-1 and strong UV-irradiation in the case of MVA) potentially resulted in selective uptake of the viruses into different cellular compartments (active virus into the cytosol and the endosome whereas uptake of inactivated virus might be restricted to the endosomal route). This could be an explanation for the complete TLR9 dependence after inactivation.

Figure 3:
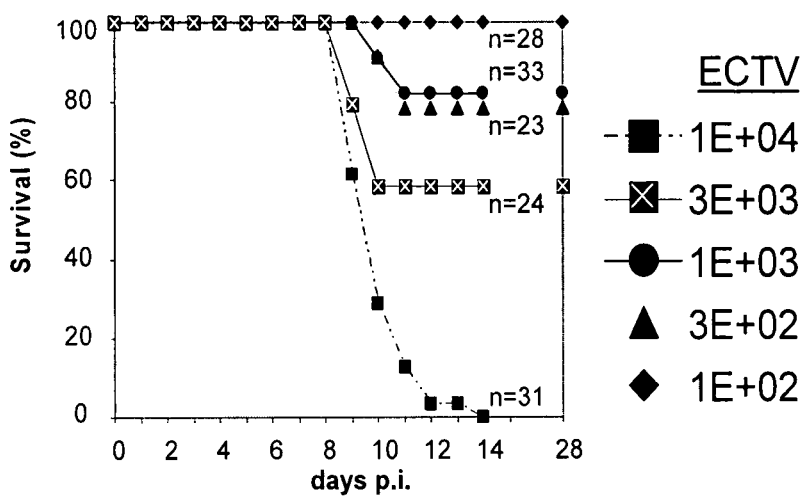
FIGS. 3a and b depict survival of wild type and TLR9-deficient mice to ECTV infection. Wild type mice (a) and TLR9-deficient mice (b) were i.n. infected with varying doses of ECTV (TCID50 per mouse) as indicated and survival was monitored for at least 4 weeks. The experiments were performed with the numbers of mice as indicated and data represent at least 3 individual experiments for each viral dose in wild type mice (a) or 7 experiments for the dose of 1E+02 for TLR9-KO mice (b) and one experiment for the other doses (b). The data for the dose of 1E+04 in wild type (a) and 1E+02 in TLR9-KO mice (b) include death control mice of other experiments.
Figure 3:
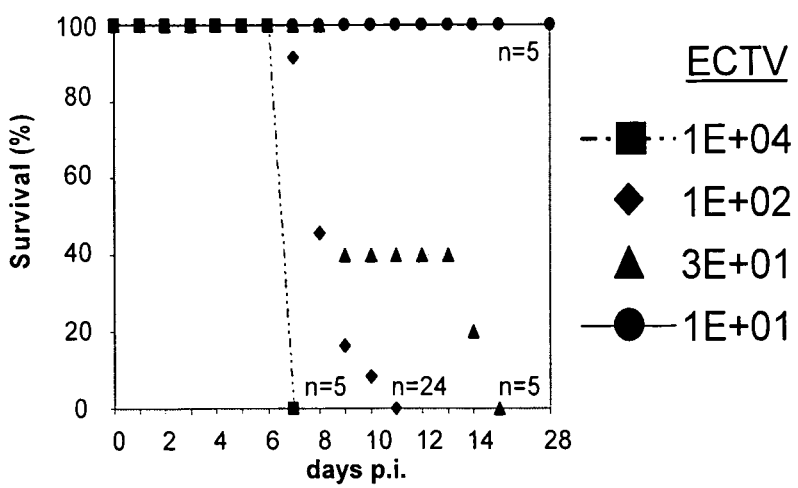

However, in sharp contrast to MVA, it is shown here that the recognition of the pathogenic poxviruses, including several strains of VACV, ECTV or CPXV critically relied on TLR9 and pDC due to the potent ability of these viruses to inhibit their recognition via TLR9-independent pathways. In the absence of pDC or TLR9, this inhibitory potential nearly completely abrogated immune recognition and thus response by DC in vitro. The in vitro findings translated into the in vivo infection model with ECTV, where TLR9-deficient mice were more than 100-fold more susceptible than wild type mice (FIG. 3). Other dsDNA virus infection models in TLR9-deficient mice have shown either no increase of susceptibility as in the case of HSV-1 infections, or only moderate increases within a narrow range in the case of MCMV infections (Krug et al., *Blood* 103:1433-1437 (2004); Tabeta et al., *Proc. Natl. Acad. Sci. U.S.A.* 101:3516-3521 (2004); Delale et al., *J. Immunol.* 175:6723-6732 (2005)).

This study defines TLR9 as an important, and in vivo highly relevant, recognition molecule for poxviruses. Importantly, it provides evidence for the use of MVA-BN as a way for immediate and therapeutic intervention against potential fatal poxvirus infection in healthy as well as immune compromised individuals.

It is a further object of the present invention to use a recombinant poxvirus, including, but not limited to an MVA virus, which can serve as an efficient and exceptionally safe expression vector. In one embodiment, the present invention relates to recombinant MVA viruses which contain a gene which codes for a foreign antigen, preferably of a pathogenic agent, and vaccines containing such a virus in a physiologically acceptable form. The invention also relates to methods for the preparation of such recombinant MVA vaccinia viruses or vaccines, and to the use of these vaccines for the prophylaxis of infections caused by such pathogenic agents.

The MVA viruses according to the invention can also be recombinant MVA expressing heterologous polypeptides. A DNA construct, which contains a DNA-sequence which codes for a foreign polypeptide flanked by MVA DNA sequences adjacent to a naturally occurring deletion, e.g. Deletion II or an IGR, within the MVA genome, can be introduced into cells infected with MVA, to allow homologous recombination. Once the DNA construct has been introduced into the eukaryotic cell and the foreign DNA has recombined with the viral DNA, it is possible to isolate the desired recombinant vaccinia virus in a manner known per se, preferably with the aid of a marker (compare Nakano et al., Proc. Natl. Acad. Sci. USA, 79:1593-1596 (1982); Franke et al., Mol. Cell. Biol, 1918-1924 (1985); Chakrabarfi et al., Mol. Cell. Biol., 3403-3409 (1985); Fathi et al., Virology 97-105 (1986)).

In one embodiment, in immune competent mice MVA immediately protects mice against the mousepoxvirus Ectromelia (>47×LD50).

In one embodiment, MVA induces immune responses in dendritic cells via TLR9 and in addition via TLR9-independent pathways. Pathogenic poxviruses like Ectromelia virus in contrast inhibit effectively the TLR9-independent recognition and thus depend on TLR9 for recognition.

In one embodiment, the immune compromised mice lacking TLR9 (TLR9-KO) have a 100-fold higher susceptibility to Ectromelia infection.

In one embodiment, MVA immediately protects TLR9-KO mice against the mouse poxvirus Ectromelia (>500×LD50).

In one embodiment, MVA protects immune compromised mice (lacking responsiveness to IFN-I) against low to intermediate challenge with Ectromelia virus (24 of 25 mice survived an otherwise deadly exposure to Ectromelia with 1E+02 or 1E+03).

In one embodiment, protection achieved by only one application of MVA is long-lasting. After 9 weeks, there is still protection against first time infection with Ectromelia (>500× LD50).

The detailed examples which follow are intended to contribute to a better understanding of the present invention. However, the invention is not limited by the examples.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

EXAMPLES

The following examples will further illustrate the present invention. It will be well understood by a person skilled in the art that the provided examples in no way may be interpreted in a way that limits the applicability of the technology provided by the present invention to these examples.

Example 1

Experimental Methods

The following section is a summary of those methods used in all of the Examples described herein.
Animal Model C57BL/6J mice were purchased from Harlan Winkelmann (Borchen, Germany). TLR9 deficient mice were generated with 129/Sv background and backcrossed to C57BL/6 for at least 8 generations as described (Hemmi, H. et al., *Nature* 408, 740-745 (2000); Hochrein, H. et al.). Both the 129/Sv as well as C57BL/6 mouse strains are regarded to display a relatively high resistance to ECTV infection (Tscharke et al., *J. Exp. Med.* 201:95-104 (2005)). However, to rule out that in the infection model the strain background would have an influence mice on the 129/Sv background were infected with ECTV i.n. and it was found that indeed they displayed the relative resistant phenotype seen in C57BL/6 mice, e.g. none of the mice died with the dose of 1E+02 TCID50 and the majority of mice even survived a dose of 3E+03. IFN-1-R deficient mice (A129) mice were originally obtained from Dr. Michel Aguet (University of Zurich) (Muller, U. et al., *Science* 264, 1918-1921 (1994)) and backcrossed to C57BL/6 mice for 8 generations. RAG-1 deficient mice were purchased from the Jackson laboratories and bred at the animal facility in Zurich.
Viruses The MVA used for this study was MVA-BN®, developed by Bavarian Nordic and deposited at European Collection of Cell Cultures (ECACC) (V00083008). MVA was propagated and titered on primary chicken embryo fibroblasts (CEF) that were prepared from 11-day-old embryonated pathogen-free hen eggs (Charles River, Mass., USA) and cultured in RPMI-1640 medium supplemented with 10% FCS. CVA and CNPV were kindly provided by Prof. A. Mayr, Veterinary Faculty, Munich, Germany and were propagated and titered on CEF. ECTV strain Moscow and CPXV strain Brighton were obtained from the American Type Culture Collection (ATCC) as VR-1372 and VR-302, respectively, and were propagated and titered on Vero C1008 cells (ECACC 85020206). SFV was obtained from ATCC (VR-364) and propagated and titered on the rabbit cornea cell line SIRC obtained from ATCC (CCL-60).

All cell lines were maintained in Dulbecco's Modified Eagle's Medium (DMEM; Invitrogen, Karlsruhe, Germany) supplemented with 10% FCS without antibiotics. All viruses used in animal experiments were purified twice through a sucrose cushion. For the UV-inactivation of viruses concentrated virus stocks were UV irradiated with an UV Chamber (Genelinker GS, Bio-Rad laboratories, Munich Germany) for 15 min under sterilizing conditions. This treatment reduced the transduction efficiency of recombinant viruses below 2% of the original virus activity.

In Vitro Experiments

In vitro generated Flt3-ligand-dependent DC (FL-DC) were generated and sorted essentially as described previously (Hochrein, H. et al., *Proc. Natl. Acad. Sci. U.S.A.* 101, 11416-11421 (2004)). In short, bone marrow cells were cultured in the presence of murine recombinant FL for eight days. Resulting cells were >90% CD11c positive and 20-60% of cells displayed plasmacytoid phenotype (CD1$1c^{pos}$CD45RA$^{high}$B220$^{high}$CD1 1b$^{low}$). FL-DC were either used unseparated or sorted into pDC and cDC using a FACS Aria instrument (BD Bioscience). In vitro generated GM-DC were generated by culturing bone marrow cells in the presence of murine recombinant GM-CSF (Tebu-bio, Offenbach, Germany) as described (Hochrein, H. et al., *Proc. Natl. Acad. Sci. U.S.A.* 101, 11416-11421 (2004)). Cells were stained with antibodies specific for CD11c, B220, CD40 and CD69 (BD Biosciences). Propidium iodide (1 µg/ml) was included in the final wash to label dead cells. Flow cytometric analyses were performed on a FACSCalibur (BD Bioscience) and analyzed with Weasel software (The Walter and Eliza Hall Institute for Medical Research, Melbourne, Australia). Cell culture supernatants were harvested 18-24 hours after incubation with the viruses as indicated or with CpG-2216 (0.5 µM or 1 µM) as control in the presence of IL-3 and GM-CSF and the secretion of IFN-[ and IL-6 was measured using commercially available ELISA-reagents as described previously (Hochrein, H. et al. (2004)).

In Vivo Experiments and Statistics

Mice were anaesthetized with ketamine/xylamine and viruses were applied by i.n. drop wise installation in a total volume of 50 µl. ECTV-dilutions as indicated were applied either alone or in combination with 1E+08 TCID$_{50}$ MVA. Subcutaneous injections were performed in the inguinal region applying a total amount of 1E+08 TCID$_{50}$ of MVA or a corresponding amount of UV-inactivated CVA by injecting 2 times a volume of 250 µl each. The health status of infected mice was checked at least daily and animals with grave symptoms of sickness or weight loss exceeding 25% were euthanized. For the determination of poxvirus specific CD8$^+$ T cell responses wild type or TLR9-deficient mice were infected intravenously with 5E+07 TCID$_{50}$ or 1E+08 TCID$_{50}$ MVA. Spleens were harvested 7 days after immunization and single cell suspensions were prepared by mechanically disrupting the organs through a 70-βm filter. Spleen cells and peripheral blood lymphocytes (PBL) were treated with red blood cell lysis buffer (0.14 M NH$_4$Cl and 0.017 M Tris-HCl, pH 7.2), washed twice, and analyzed. Cells were stained with Pro5® H-2 Kb Pentamers (ProImmune, Oxford, UK) loaded with the immunodominant B8R peptide TSYKFESV (Tscharke et al., *J. Exp. Med.* 201:95-104 (2005)). Pentamer staining was performed in combination with anti-CD8, anti-CD 19 and anti-NK1 1 antibodies according to the manufacturers' protocol. For intracellular cytokine staining cell suspensions were stimulated for 5 hrs with 1 µg/ml B8R peptide in the presence of 1 µg/ml GolgiPlug (BD Biosciences). Afterward, cells were surface stained with anti-CD8 and then simultaneously fixed/permeabilized with the BD Cytofix/Cytoperm Kit (BD Biosciences) and finally stained with antibodies directed against IFN-α, TNF-I and IL-2. Poxvirus specific antibodies in sera were measured by ELISA using MVA crude extract as antigen and a sheep-anti-mouse-IgG-HRP (Serotec, Germany) as detection antibody. All animal experiments were approved by the government of Bavaria. For the calculation of the $_{LD50}$, the Spearman-Karber method was used.

Example 2

Inactivation of VACV, CPXV and ECTV but not of MVA, CNPV and SFV Increases DC Maturation Previously it has been described that several strains of VACV inhibit the maturation of cDC whereas maturation occurred in response to MVA (Engelmayer et al., *J. Immunol.* 163:6762-6768 (1999); Drillien et al., *J. Gen. Virol.* 85:2167-2175 (2004)). Since these studies analyzed only the role of cDC in the absence of pDC Flt3-ligand (FL)-generated murine DC were employed, that consist of DC that closely resemble ex-vivo mouse spleen cDC and pDC (Naik et al., *J. Immunol.* 174:6592-6597 (2005)), to examine the activation of both DC types. To test whether different stimulatory activities of different VACV were due to lack of stimulus or active inhibition by a virus-encoded component, FL-DC were incubated with several different strains of poxviruses either as active virus or after UV-inactivation. The activation of DC in response to VACV strain Ankara (CVA), ECTV and CPXV was amplified after viral UV-inactivation compared to the activation of DC in response to active viruses (FIG. 1*a*). These initial data indicated an inhibitory component, acting on DC, was made by those viruses. In contrast, DC activation as measured by the upregulation of CD40, CD69 and CD86 in response to MVA as well as the canarypox virus (CNPV) and rabbit Shope fibroma virus (SFV) was not increased after UV-inactivation (FIG. 1*b* and data not shown), suggesting that these viruses lacked an active inhibitory component. Apart from DC maturation, the production of cytokines including IFN-α and IL-6 increased after the UV-inactivation of CVA, ECTV and CPXV but not of MVA, CNPV and SFV, suggesting a broad inhibition of viral recognition and DC function, not restricted to maturation.

Example 3

Recognition of CVA and ECTV but not of MVA Exclusively Depends on TLR9

It has previously been shown that dsDNA viruses like herpesviruses or adenoviruses could be recognized via TLR9-dependent as well as TLR9-independent recognition pathways (Basner-Tschakarjan et al., *J. Gene Med.* 8:1300-1306 (2006); Hochrein et al., *Proc. Natl. Acad. Sci. U.S.A.* 101:11416-11421 (2004)). To elucidate the role of TLR9 in the recognition of poxviruses FL-DC of wild type or TLR9-deficient animals were generated. In the absence of TLR9, DC did not significantly mature in response to active CVA or ECTV, as monitored by the lack of upregulation of CD40 and CD69, indicating a strong dependence upon TLR9 for the recognition of these viruses. However, in the absence of TLR9 MVA induced robust upregulation of CD69 but a drastically reduced upregulation of CD40 (FIG. 2*a*), suggesting that the response to MVA is based on both TLR9-independent and TLR9-dependent recognition events.

FL-DC contain both pDC, known as the sole cell type producing large amounts of IFN-α in response to TLR9 activation, and cDC, known to be unable to produce large scale IFN-α production in response to TLR9. FL-DC of wild type and TLR9-deficient mice were incubated with active MVA and produced dose-dependent robust amounts of IFN-α and IL-6 demonstrating the existence of a TLR9-independent recognition pathway for MVA (FIG. 2b). However, UV-inactivated MVA induced IFN-α and IL-6 solely in wild type but not in TLR9 deficient FL-DC, reinforcing the notion suggested by the maturation data, that the recognition of MVA also employed a TLR9-dependent component (FIG. 2b).

Figure 2C:
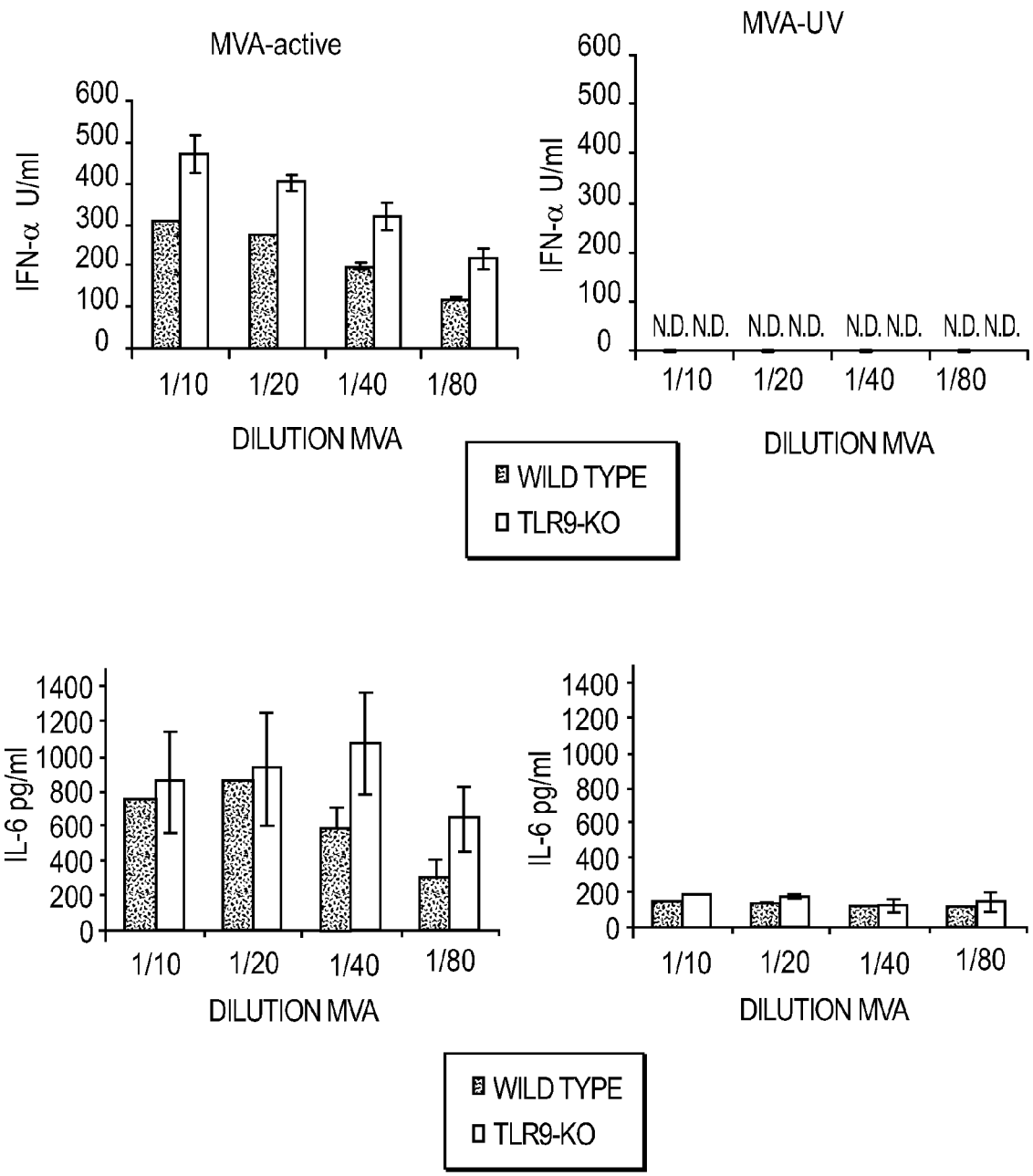

DC generated in vitro with GM-C SF resulted in a DC population (GM-DC) of only cDC which are able to produce IFN-α in response to active DNA viruses (e.g. Herpes simplex virus (HSV)) but not to inactivated viruses or CpG-ODN (Hochrein et al., *Proc. Natl. Acad. Sci. U.S.A.* 101:11416-11421 (2004)). Incubation of GM-DC with active MVA induced IFN-α and IL-6 production in wild type and TLR9-deficient cells, demonstrating the TLR9-independent recognition of active MVA. No IFN-α production and no IL-6 above constitutive levels produced was detected after incubation with UV-inactivated MVA (FIG. 2c) potentially indicating that the TLR9-dependent recognition in response to MVA is not functional in those cells.

Example 4

Recognition of ECTV but not of MVA Exclusively Depends on TLR9 and pDC

Figure 2D:
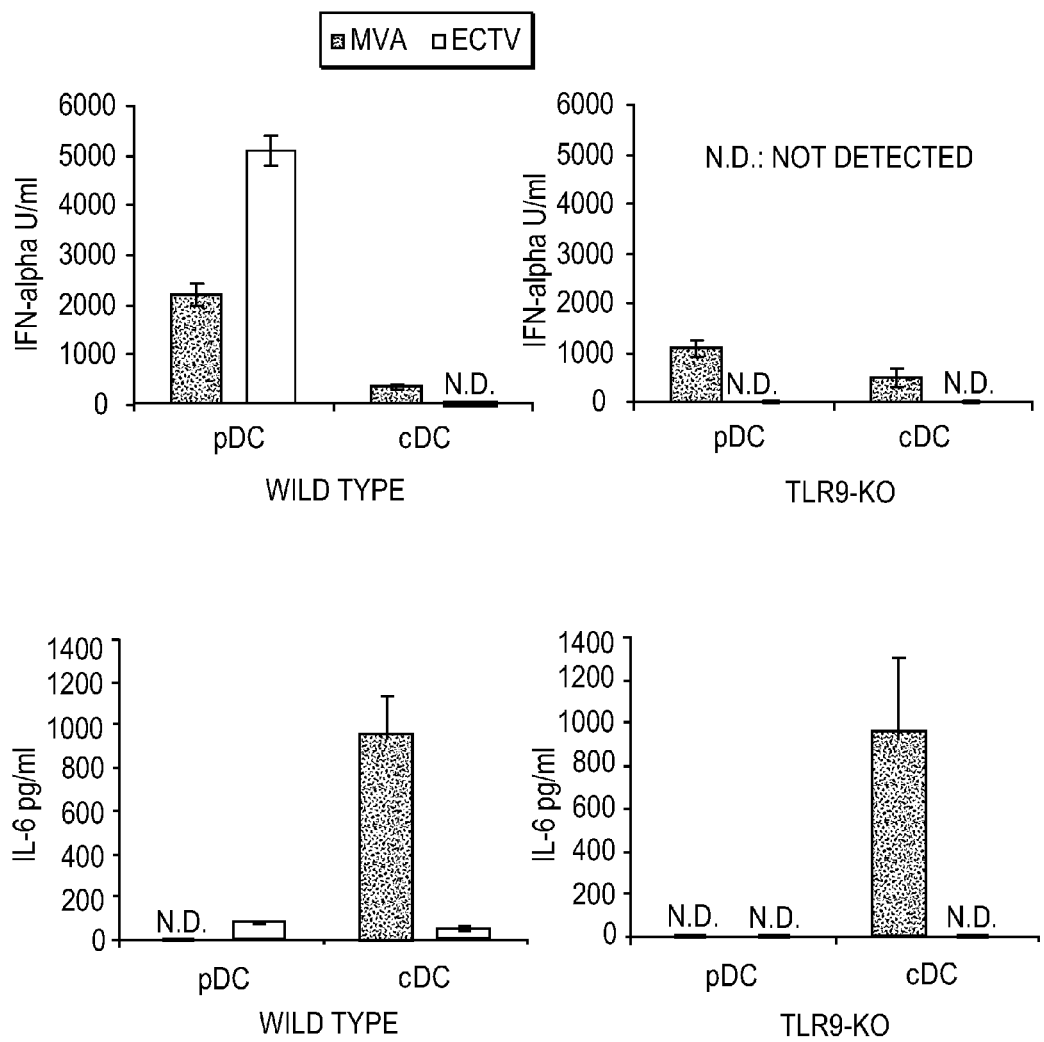

To define the individual activation profiles of the two main DC subsets among the FL-DC pDC and cDC were sorted, infected with ECTV and MVA, and the IFN-α and IL-6 production was measured. Wild type pDC produced IFN-α to both ECTV and MVA and very little IL-6 to ECTV. However cDC or TLR9-deficient pDC only produced IFN-α in response to MVA but not ECTV (FIG. 2d). Wild type and TLR9-deficient cDC also produced large amounts of IL-6 in response to MVA but not to ECTV. These results strengthen the observations obtained with DC maturation (FIG. 2a) and demonstrate that effective recognition of ECTV depends on the presence of TLR9, and in particular that IFN-α production by ECTV is dependent upon pDC. ECTV clearly inhibits recognition via other TLR9-independent pathways. On the other hand, recognition of MVA by both pDC and cDC is composed of an additional TLR9-independent mechanism.

Figure 2E:
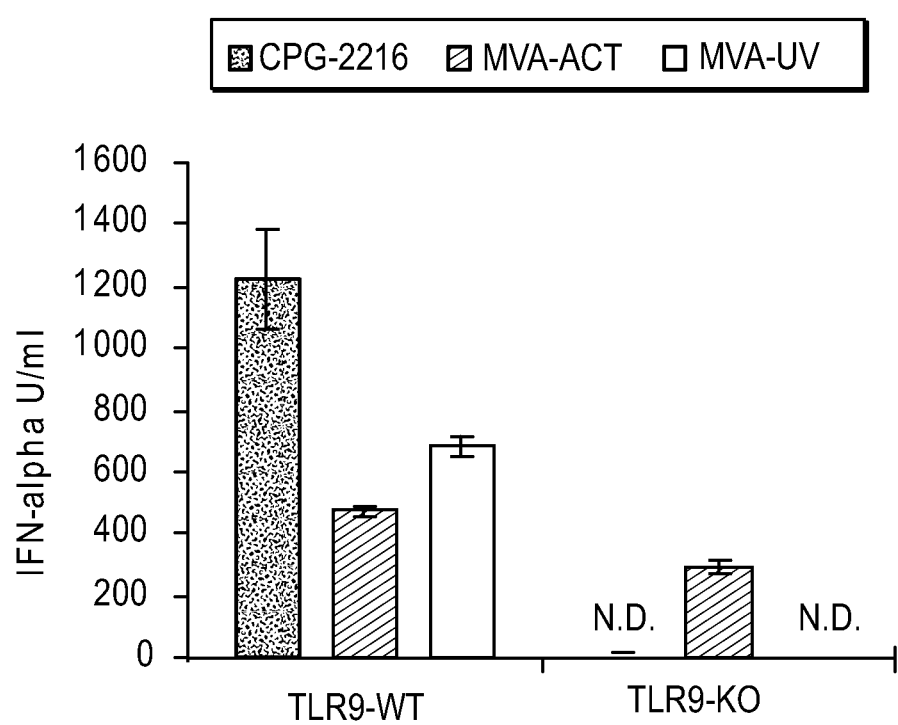

To analyze ex vivo isolated pDC containing cell populations in addition to in vitro generated FL-DC, wild type and TLR9-deficient total bone marrow cells, a rich source of pDC in vivo, were stimulated with active or UV-inactivated MVA in parallel to CpG-ODN as a control. Similar to results with FL-DC, active MVA induced robust IFN-α production in wild type and TLR9-deficient bone marrow cells, whereas with the lack of TLR9 the IFN-α production in response to UV-inactivated MVA and CpG-ODN was completely abrogated (FIG. 2e). Thus, these data demonstrated that MVA was recognized by freshly isolated bone marrow cells via a UV-sensitive TLR9-independent pathway and a TLR9-dependent pathway.

Example 5

TLR9-Deficient Mice have a Drastically Increased Susceptibility to ECTV Infection Previous reports have clearly demonstrated the recognition of DNA viruses by TLR9 in vitro but the in vivo relevance of TLR9 for the survival of mice is less clear. TLR9-deficient mice showed either no difference in survival in infection models using HSV or, limited survival differences within a narrow range, in infection models using mouse cytomegalovirus (MCMV) (Krug et al., *Blood* 103:1433-1437 (2004); Tabeta et al., *Proc. Natl. Acad. Sci. U.S.A.* 101:3516-3521 (2004); Delale et al., *J. Immunol.* 175:6723-6732 (2005)). Given the strong suppression of TLR9-independent recognition in vitro by poxviruses like ECTV (FIG. 1, FIG. 2), it was hypothesized that TLR9 would be an important factor for the survival of infection with these viruses. To test this, a mouse infection model that mimicked as closely as possible a human smallpox infection was used: an ECTV infection model via the intranasal route. Similar to VARV infection in humans, ECTV is highly species specific and is a natural mouse pathogen, able to effectively infect via the respiratory tract after exposure with only small viral doses. In addition, it carries a large panel of immune suppressive molecules similar to VARV (Esteban, D. J., and Buller, R. M., *J. Gen. Virol.* 86:2645-2659 (2005)).

Initial experiments using relatively high doses of ECTV (1E+04 tissue culture infective doses ($TCID_{50}$)) demonstrated that TLR9-deficient mice died at least 2 days earlier than wild type mice. To further evaluate the susceptibility and quantify the $LD_{50}$ TLR9-deficient and wild type mice were infected with varying doses of ECTV. All TLR9-deficient mice died after infection with as little as 3E+01 $TCID_{50}$ whereas none died after inoculation with 1E+01 $TCID_{50}$ (FIG. 3b). In contrast, none of the wild type mice died after infection with 1E+02 $TCID_{50}$ and only when using 1E+04 $TCID_{50}$ all mice succumbed to Ectromelia infection (FIG. 3a). There was some variation between experiments with wild type mice using the doses of 3E+02 to 3E+03 $TCID_{50}$, which was partially gender-specific, with male mice being more susceptible than female mice. An $LD_{50}$ of 19 $TCID_{50}$ for the TLR9-deficient mice and an $LD_{50}$ of about 2120 $TCID_{50}$ for the wild type mice was calculated. Thus, TLR9-deficient mice are more than 100-fold more susceptible to ECTV infection than wild type mice. Therefore, in strong agreement with the in vitro data, TLR9 is an essential component of the immune response to ECTV infection.

Example 6

Figure 4:
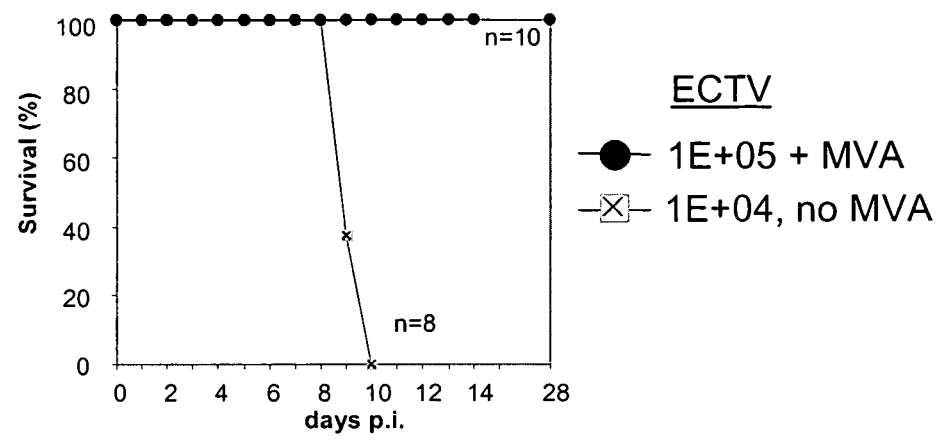

MVA Immediately Protects Wild Type and TLR9-Deficient Mice from Lethal ECTV Challenge In vitro experiments demonstrated that ECTV effectively suppressed recognition by DC, whereas MVA activated DC (FIG. 1). It was therefore hypothesized that MVA given at the same time as the pathogen would activate the immune system and as a result might induce immune responses which potentially control the pathogenic poxvirus. Indeed, MVA given at the same time or immediately after challenge with a high lethal dose of ECTV of 1E+05 $TCID_{50}$ completely protected wild type mice against death whereas all control mice died with the 10-fold lower dose of 1E+04 $TCID_{50}$ (FIG. 4).

Figure 5:
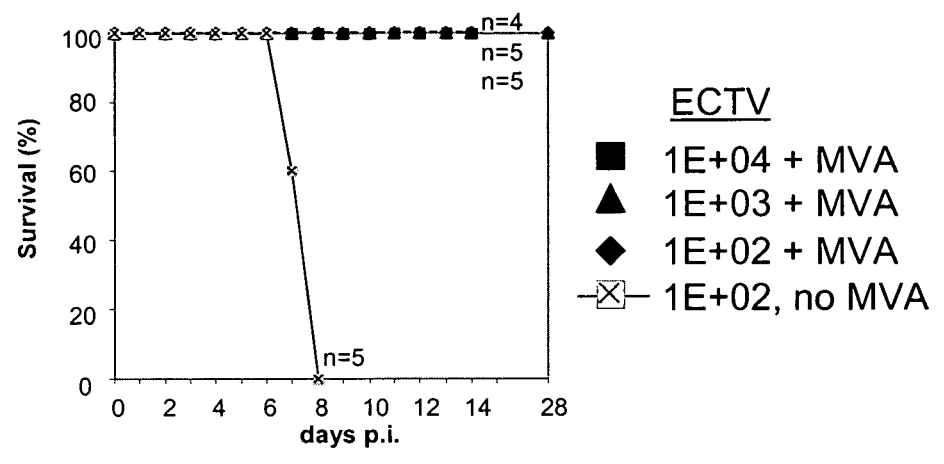

Since MVA induced a strong TLR9-independent activation of immune cells in vitro, whether MVA could protect TLR9-deficient mice against ECTV infection was tested next. Similar to the protection seen in wild type mice (FIG. 4), MVA immediately protected TLR9-deficient mice against highly lethal doses of ECTV infection. Whereas all untreated control mice died with 1E+02 $TCID_{50}$, all MVA treated mice even survived a challenge with 1E+04 $TCID_{50}$, which resembles a dose exceeding 500-fold the $LD_{50}$ for TLR9-deficient mice (FIG. 5). It was observed that TLR9-deficient mice challenged with high doses of ECTV (3E+03 and 1E+04 $TCID_{50}$) developed tail lesions after 2-3 weeks which disappeared after 4 weeks. The tail lesions on otherwise symptom free TLR9-deficient mice indicated that MVA-induced immune responses were able to prevent severe ECTV-induced disease and death, but not to completely eliminate the virus within the first weeks.

Example 7

Mice can be Protected Against Lethal ECTV Infection if MVA is Applied to a Different Site To ascertain whether the immediate protection in wild type and TLR9-deficient mice was absolutely dependent on the coadministration of MVA to the same site as the ECTV infection mice were challenged intranasally with a lethal dose of ECTV and applied MVA via a subcutaneous injection. The TLR9-deficient (FIG. 6*a*) and wild type mice (FIG. 6*b*) survived the lethal ECTV infection, without any signs of sickness, if MVA was applied to the subcutaneous site (FIG. 6). Thus coadministration of MVA to the same site as ECTV was not essential for immediate protection.

Example 8

Inactivated Orthopoxviruses are Less Efficient than MVA in Protection from Lethal ECTV Infection Our in vitro experiments have suggested that UV-inactivated orthopoxviruses act as exclusive TLR9 agonists but have lost their ability to stimulate via a TLR9-independent way (FIG. 2). To test if this 'TLR-9 only' stimulation in the presence of orthopoxvirus-antigen would mount any protection wild type mice were challenged with a lethal dose of ECTV and applied subcutaneously the equivalent of 1E+08 $TCID_{50}$ of a UV-inactivated CVA. Of the 5 mice challenged one died on day 11 whereas the others survived (FIG. 6*b*). However in contrast to the mire which received the same dose of active MVA subcutaneously, all mice treated with inactivated CVA showed strong signs of sickness including lethargy and they developed tail lesions which healed only in the $4^{th}$ week of challenge. Thus inactivated orthopoxviruses, although providing viral antigen and potential TLR9 ligand, seem to induce protection that is inferior to the robust protection achieved with active MVA.

Example 9

MVA Mediated Immediate Protection from Lethal ECTV Challenge is Partially Independent of IFN-I To elucidate if administration of MVA was able to immediately protect other immune compromised mice and to shed light on the mechanism of protection experiments were performed with IFN-I receptor (IFN-I-R)-deficient mice, which are known to be highly susceptible to several viral infections including poxvirus infections (26). Initial experiments demonstrated that similar to TLR9-deficient mice all IFN-I-R-deficient mice died after challenge with 1E+02 $TCID_{50}$ of ECTV. Since the IFN-$\alpha$ production in vitro to ECTV but not to MVA was dependent on TLR9, it was hypothesized that MVA induced IFN-$\alpha$ was an essential part of the immediate protection in TLR9-deficient mice. However, whereas the untreated control IFN-I-R-deficient mice died with a challenge of 1E+02 $TCID_{50}$ ECTV within 10 days, immediate MVA treatment surprisingly protected the IFN-I-R-deficient mice against a challenge with 1E+02 and 1E+03 $TCID_{50}$ ECTV (FIG. 7). From a total of 15 IFN-I-R mice challenged with 1E+02 $TCID_{50}$ of ECTV, one mouse developed a swollen limb and had to be euthanized after 3 weeks for ethical reasons, whereas the other 14 mice and all 10 mice challenged with 1E+03 ECTV were free of symptoms for more than 4 weeks. However with higher doses of ECTV the protection of IFN-IR-deficient mice was much less robust. About half of the IFN-I-R mice challenged with 1E+04 ECTV died and all IFN-I-R mice challenged with 1E+05 ECTV died (FIG. 7). Since these higher doses correspond to viral challenges that wild type mice on the same background could survive in the presence of MVA, it was concluded that one mechanism of the immediate protection via MVA is mediated by IFN-I. However, some protection is clearly mediated via IFN-I-independent mechanisms since MVA could protect mice against low and intermediate doses of lethal ECTV infection even in the absence of a functional IFN-I system.

Example 10

The Immediate Protection Via MVA in ECTV Infection Depends on Adaptive Immune Responses MVA is known to induce strong adaptive immune responses including cytotoxic T-cell (CTL) responses and antibody formation which both contribute to the protection against pathogenic orthopoxviruses (Wyatt et al., *Proc. Natl. Acad. Sci. U.S.A.* 101:4590-4595 (2004)). Previously, it has been shown that TLR9-deficient mice are able to mount stable CTL and antibody responses upon DNA vaccination, thus demonstrating the overall capability of these mice to mount solid adaptive immune responses (Spies et al., *J. Immunol.* 171:5908-5912 (2003); Babiuk et al., *Immunology* 113:114-120 (2004)).

To test if the absence of TLR9 would affect adaptive immune responses to poxviruses MVA was applied and antibodies to poxviruses were measured by ELISA in the serum and poxvirus specific CTL responses by pentamer staining to B8R in spleen cells and peripheral blood cells. TLR9-deficient mice mounted robust poxvirus specific antibody and CTL responses indicating that adaptive immune responses in response to MVA vaccination are not dependent on the presence of TLR9.

It was next investigated if the measured adaptive immune responses would translate into long lasting protection to ECTV infection, thus whether the MVA-induced protection in TLR9-deficient mice was not only immediate (FIG. 5), but also long-lasting. Nine weeks after initial challenge, the TLR9-deficient mice from the experiments described above (FIG. 5) and in addition mice that had received MVA alone nine weeks earlier were re-challenged using 1E+04 $TCID_{50}$ of ECTV. All TLR9-deficient mice which had received a single dose of MVA nine weeks earlier either alone or in combination with ECTV survived the challenge with 1E+04 $TCID_{50}$ of ECTV. As observed with the immediate protection, the long lasting protection of the TLR9-deficient mice after MVA treatment exceeded a factor of 500 of the $_{LD50}$. These experiments demonstrated that TLR9-deficient mice were capable of mounting and sustaining substantial protective immunity to poxvirus infection upon traditional vaccination with MVA which most likely depended on adaptive immune responses.

To prove the role of adaptive immune responses in the immediate protection protocol Rag-1 deficient mice were challenged with ECTV in the presence or absence of MVA (FIG. 8). Rag-1 deficient mice lack mature B-cells and T-cells and thus are unable to produce antibodies and CTL. Without co administration of MVA Rag-1 deficient mice died rapidly in response to ECTV challenge (1E+02 and 1E+03). Cotreatment with MVA extended the survival of Rag-1 mice for several days, but finally all mice died, demonstrating that adaptive immune responses are indeed crucial for the survival of ECTV, even in the presence of immediately applied MVA.

Example 11

MVA Fully Rescues TLR9-Deficient Mice if Applied Two Days after Infection with ECTV The WHO recommendation in cases of smallpox infection includes vaccination as quickly as possible after exposure. However there exists only anecdotal historical information about the success of post-exposure vaccination against smallpox and in most cases the pre-vaccination status of the individuals was not clear. (Fenner, F., Henderson, D. A., Arita, I., Jezek, Z., & Ladnyi, I. D. *Smallpox and its eradication.* (Geneva: World Health Organization; 1988); Mortimer, P. P., *Clin. Infect. Dis.* 36, 622-629 (2003)). Moreover, in animal models no significant survival benefit to post-exposure vaccination was observed using as infection models either the MPXV in monkeys or VACV in mice (Stittelaar et al., *Nature* 439:745-748 (2006); Staib et al., *J. Gen. Virol.* 87:2917-2921 (2006)). In this way, the results of the current invention are unexpected.

Figure 9:
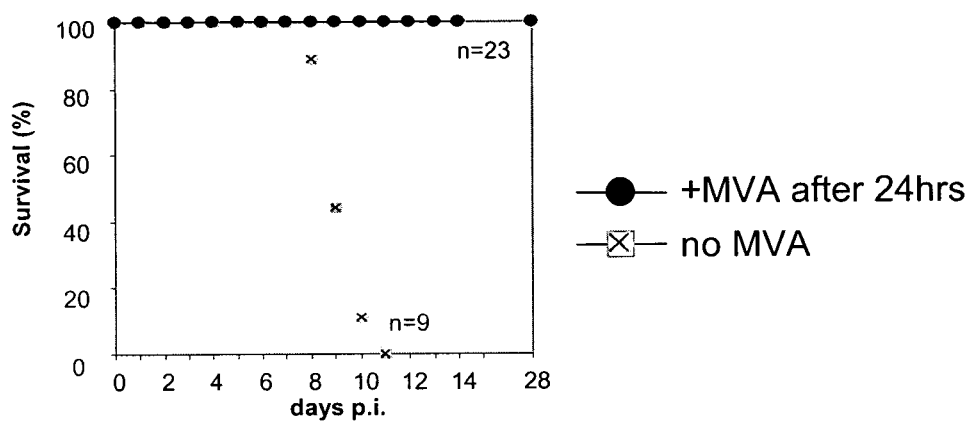
FIGS. 9 a and b depict that MVA therapeutically protects TLR9-deficient mice if applied after infection with a lethal dose of ECTV. TLR9-deficient mice were i.n. infected with 1E+02 TCID$_{50}$ ECTV. After the indicated times of 24 hrs (a) or 48 hrs or 72 hrs (b) the ECTV infected mice were i.n. inoculated with 1E+08 TCID$_{50}$ of MVA (black symbols) or without (grey square) and survival was monitored for 4 weeks. The experiments were performed with the numbers of mice as indicated and data show the cumulated results of 3 individual experiments (a) or one experiment (b). Note that the 9 control mice of a) include the 3 control mice of b).
Figure 9:
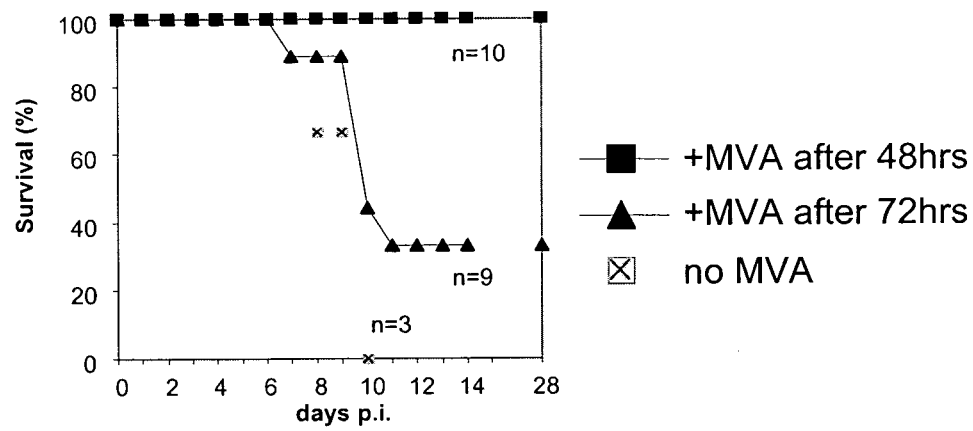

Given this scenario and the fact that the intranasal infection model of ECTV is regarded as a good animal model for smallpox infection in humans (Esteban, D. J., and Buller, R. M., *J. Gen. Virol.* 86:2645-2659 (2005)), whether the robust immediate protection against a lethal ECTV infection by MVA could be extended to a therapeutic post-exposure intervention with MVA was analyzed. As shown in FIG. 9, MVA given up to two days after exposure to a lethal dose of ECTV, completely protected TLR9-deficient mice against death without any obvious signs of sickness (FIG. 9 and data not shown). Some mice in the group which received MVA treatment as late as 3 days after a lethal dose of ECTV also survived (FIG. 9b). These data show protection against death to species-specific orthopoxvirus infection using as a post-exposure treatment.

The invention claimed is:

1. A method for inducing a protective immune response against a replication competent poxvirus in a human, comprising administering to the human an immunogenic composition comprising a modified Vaccinia Ankara (MVA) virus within 72 hours after exposure to the replication competent poxvirus, wherein the administration of the immunogenic composition induces a protective immune response against the replication competent poxvirus in the human.

2. The method of claim 1, wherein the immunogenic composition comprising an MVA virus is administered within 48 hours after exposure to the replication competent poxvirus.

3. The method of claim 2, wherein the immunogenic composition comprising an MVA virus is administered within 24 hours after exposure to the replication competent poxvirus.

4. The method of claim 1, wherein the replication competent poxvirus is a Variola virus.

5. The method of claim 1, wherein the replication competent poxvirus is a Variola virus.

6. The method of claim 3, wherein the replication competent poxvirus is a Variola virus.

7. The method of claim 1, wherein the MVA virus is administered in a dose of $10^8$ to $5 \times 10^8$ $TCID_{50}$.

8. The method of claim 2, wherein the MVA virus is administered in a dose of $10^8$ to $5 \times 10^8$ $TCID_{50}$.

9. The method of claim 3, wherein the MVA virus is administered in a dose of $10^8$ to $5 \times 10^8$ $TCID_{50}$.

10. The method of claim 4, wherein the MVA virus is administered in a dose of $10^8$ to $5 \times 10^8$ $TCID_{50}$.

11. The method of claim 5, wherein the MVA virus is administered in a dose of $10^8$ to $5 \times 10^8$ $TCID_{50}$.

12. The method of claim 6, wherein the MVA virus is administered in a dose of $10^8$ to $5 \times 10^8$ $TCID_{50}$.

13. The method of claim 7, wherein the MVA virus is MVA-BN.

14. The method of claim 8, wherein the MVA virus is MVA-BN.

15. The method of claim 9, wherein the MVA virus is MVA-BN.

16. The method of claim 10, wherein the MVA virus is MVA-BN.

17. The method of claim 11, wherein the MVA virus is MVA-BN.

18. The method of claim 12, wherein the MVA virus is MVA-BN.

* * * * *